US011992490B2

United States Patent
Smith et al.

(10) Patent No.: US 11,992,490 B2
(45) Date of Patent: May 28, 2024

(54) USE OF JAK1 INHIBITORS FOR THE TREATMENT OF CUTANEOUS LUPUS ERYTHEMATOSUS AND LICHEN PLANUS (LP)

(71) Applicant: Incyte Corporation, Wilmington, DE (US)

(72) Inventors: Paul Smith, Wilmington, DE (US); Jörg Wenzel, Bonn (DE)

(73) Assignee: Incyte Corporation, Wilmington, DE (US)

( * ) Notice: Subject to any disclaimer, the term of this patent is extended or adjusted under 35 U.S.C. 154(b) by 189 days.

(21) Appl. No.: 17/072,093

(22) Filed: Oct. 16, 2020

(65) Prior Publication Data

US 2021/0113566 A1   Apr. 22, 2021

Related U.S. Application Data

(60) Provisional application No. 62/915,833, filed on Oct. 16, 2019.

(51) Int. Cl.
| | |
|---|---|
| *A61K 31/519* | (2006.01) |
| *A61K 31/4155* | (2006.01) |
| *A61K 31/437* | (2006.01) |
| *A61P 17/00* | (2006.01) |
| *A61K 9/00* | (2006.01) |
| *A61K 45/06* | (2006.01) |

(52) U.S. Cl.
CPC ........ *A61K 31/519* (2013.01); *A61K 31/4155* (2013.01); *A61K 31/437* (2013.01); *A61P 17/00* (2018.01); *A61K 9/0014* (2013.01); *A61K 9/0053* (2013.01); *A61K 45/06* (2013.01)

(58) Field of Classification Search
CPC .............. A61K 31/519; A61K 31/4155; A61K 31/437; A61K 9/0014; A61K 9/0053
See application file for complete search history.

(56) References Cited

U.S. PATENT DOCUMENTS

| | | | |
|---|---|---|---|
| 5,521,184 | A | 5/1996 | Zimmerman |
| 7,598,257 | B2 | 10/2009 | Rodgers et al. |
| 8,691,807 | B2 | 4/2014 | Yao et al. |
| 8,716,303 | B2 | 5/2014 | Rodgers et al. |
| 8,722,693 | B2 | 5/2014 | Rodgers et al. |
| 8,765,734 | B2 | 7/2014 | Huang et al. |
| 8,933,085 | B2 | 1/2015 | Rodgers et al. |

(Continued)

FOREIGN PATENT DOCUMENTS

| | | |
|---|---|---|
| JP | 2013522214 | 6/2013 |
| JP | 2015535288 | 12/2015 |

(Continued)

OTHER PUBLICATIONS

Bohm, Experimental Dermatology. 2017;26:728-747 (Year: 2017).*

(Continued)

*Primary Examiner* — San Ming R Hui
(74) *Attorney, Agent, or Firm* — Fish & Richardson P.C.

(57) ABSTRACT

The present application provides methods of treating a disease selected from cutaneous lupus erythematosus (CLE) and Lichen planus (LP) in a patient in need thereof, comprising administering to the patient a therapeutically effective amount of a JAK1 selective inhibitor, or a pharmaceutically acceptable salt thereof.

16 Claims, 5 Drawing Sheets

(56) References Cited

U.S. PATENT DOCUMENTS

| | | |
|---|---|---|
| 8,987,443 B2 | 3/2015 | Liu et al. |
| 9,023,840 B2 | 5/2015 | Yao et al. |
| 9,034,884 B2 | 5/2015 | Rodgers et al. |
| 9,181,271 B2 | 11/2015 | Li et al. |
| 9,193,733 B2 | 11/2015 | Rodgers et al. |
| 9,221,845 B2 | 12/2015 | Liu et al. |
| 9,249,145 B2 | 2/2016 | Rodgers et al. |
| 9,249,149 B2 | 2/2016 | Silverman et al. |
| 9,334,274 B2 | 5/2016 | Rodgers et al. |
| 9,359,358 B2 | 6/2016 | Rodgers et al. |
| 9,382,231 B2 | 7/2016 | Li et al. |
| 9,464,088 B2 | 10/2016 | Huang et al. |
| 9,487,521 B2 | 11/2016 | Zhou et al. |
| 9,498,467 B2 | 11/2016 | Leopold et al. |
| 9,540,367 B2 | 1/2017 | Tung |
| 9,611,269 B2 | 4/2017 | Yao et al. |
| 9,655,854 B2 | 5/2017 | Yeleswaram et al. |
| 9,714,233 B2 | 7/2017 | Liu et al. |
| 9,718,834 B2 | 8/2017 | Zhou et al. |
| 9,777,017 B2 | 10/2017 | Li et al. |
| 9,802,957 B2 | 10/2017 | Zhou et al. |
| 9,908,895 B2 | 3/2018 | Li et al. |
| 9,926,301 B2 | 3/2018 | Li et al. |
| 9,999,619 B2 | 6/2018 | Huang et al. |
| 10,370,387 B2 | 8/2019 | Li et al. |
| 10,435,392 B2 | 10/2019 | Li et al. |
| 10,450,325 B2 | 10/2019 | Zhou et al. |
| 10,513,522 B2 | 12/2019 | Yao et al. |
| 10,561,616 B2 | 2/2020 | Yeleswaram et al. |
| 10,640,506 B2 | 5/2020 | Rodgers et al. |
| 10,695,337 B2 | 6/2020 | Huang et al. |
| 10,899,736 B2 | 1/2021 | Wang et al. |
| 11,001,571 B2 | 5/2021 | Li et al. |
| 11,045,421 B2 | 6/2021 | Yeleswaram et al. |
| 11,103,510 B2 | 8/2021 | Montgomery et al. |
| 11,161,855 B2 | 11/2021 | Li et al. |
| 11,214,573 B2 | 1/2022 | Yao et al. |
| 11,285,140 B2 | 3/2022 | Huang et al. |
| 11,304,949 B2 | 4/2022 | Howell et al. |
| 11,324,749 B2 | 5/2022 | Assad |
| 11,406,640 B2 | 8/2022 | Shaub et al. |
| 2007/0225286 A1 | 9/2007 | Ren et al. |
| 2010/0298334 A1 | 11/2010 | Rodgers et al. |
| 2011/0059951 A1 | 3/2011 | Rodgers et al. |
| 2011/0224190 A1* | 9/2011 | Huang ............... A61K 9/0048 544/405 |
| 2012/0149682 A1 | 1/2012 | Rodgers et al. |
| 2012/0149681 A1 | 6/2012 | Rodgers et al. |
| 2013/0018034 A1 | 1/2013 | Yao et al. |
| 2013/0045963 A1 | 2/2013 | Rodgers et al. |
| 2013/0060026 A1 | 3/2013 | Zhou et al. |
| 2014/0005166 A1 | 1/2014 | Rodgers et al. |
| 2014/0121198 A1 | 5/2014 | Li et al. |
| 2014/0256941 A1 | 9/2014 | Liu et al. |
| 2014/0343030 A1 | 11/2014 | Li et al. |
| 2015/0087632 A1 | 3/2015 | Rodgers et al. |
| 2015/0246046 A1 | 9/2015 | Vaddi |
| 2015/0344497 A1 | 12/2015 | Zhou et al. |
| 2019/0111058 A1 | 4/2019 | Vaddi |
| 2020/0197399 A1 | 6/2020 | Yeleswaram et al. |
| 2021/0069193 A1 | 3/2021 | Vaddi |
| 2021/0238168 A1 | 8/2021 | Li et al. |
| 2021/0380563 A1 | 12/2021 | Zhou et al. |
| 2021/0387998 A1 | 12/2021 | Li et al. |
| 2022/0016036 A1 | 1/2022 | Yeleswaram et al. |
| 2022/0040187 A1 | 2/2022 | Montgomery et al. |
| 2022/0056034 A1 | 2/2022 | Zhou et al. |
| 2022/0175731 A1 | 6/2022 | Smith et al. |
| 2022/0226327 A1 | 7/2022 | Peel et al. |
| 2022/0241286 A1 | 8/2022 | Howell et al. |

FOREIGN PATENT DOCUMENTS

| | | |
|---|---|---|
| JP | 2016519147 | 6/2016 |
| JP | 2019506422 | 3/2019 |
| WO | WO 2000/009495 | 2/2000 |
| WO | WO 2000/053595 | 9/2000 |
| WO | WO 2001/014402 | 3/2001 |
| WO | WO 2001/064655 | 9/2001 |
| WO | WO 2002/000196 | 1/2002 |
| WO | WO 2003/024967 | 3/2003 |
| WO | WO 2003/037347 | 5/2003 |
| WO | WO 2003/099771 | 12/2003 |
| WO | WO 2004/005281 | 1/2004 |
| WO | WO 2004/046120 | 6/2004 |
| WO | WO 2004/056786 | 7/2004 |
| WO | WO 2004/080980 | 9/2004 |
| WO | WO 2005/028444 | 3/2005 |
| WO | WO 2006/056399 | 6/2006 |
| WO | 2010020905 A1 | 2/2010 |
| WO | 2012003829 A1 | 1/2012 |
| WO | 2014015107 A1 | 1/2014 |
| WO | 2016027195 A1 | 2/2016 |
| WO | 2018087202 A1 | 5/2018 |
| WO | 2019191679 A1 | 10/2019 |

OTHER PUBLICATIONS

International Search Report and Written Report for PCT/US2019/056533 dated Jun. 12, 2020.

Inacio, "Cutaneous Lupus Erythematosus Patients May Benefit from JAK1 Inihibitors", https://lupusnewstoday.com/2016/10/17/jak1-inhibitors-may-prove-beneficial-cutaneous-lupus-erythematosus (retrieved Mar. 23, 2018].

Kuhn et al., "Advances in the treatment of cutaneous lupus erythematosus" Lupus, vol. 25, No. 8, May 31, 2016, pp. 830-837.

Albrecht et al., "The CLASI (Cutaneous Lupus Erythematosus Disease Area and Severity Index): an outcome instrument for cutaneous lupus erythematosus," J Invest Dermatol., 2005, 125:889-894.

Alves de Medeiros et al., "JAK3 as an Emerging Target for Topical Treatment of Inflammatory Skin Diseases," PLoS ONE., 2016, 11:e0164080.

Arrue et al., "Lupus-like reaction to interferon at the injection site: report of five cases," J Cutan Pathol., 2007, 34 Suppl I: 18-21.

Atzrodt, "The Renaissance of H/D Exchange," Angew Chem Int Ed., 2007, 46(41):7744-7765.

Banerjee et al., "JAK-STAT Signaling as a Target for Inflammatory and Autoimmune Diseases: Current and Future Prospects," Drugs, 2017, 77:521-546.

Berge et al., "Pharmaceutical Salts," Journal of Pharmaceutical Science, 1977, 66:1-19.

Briand et al., "Efficacy of JAK1/2 inhibition in the treatment of chilblain lupus due to TREX1 deficiency," Ann Rheum Dis., 2019, 78:431-433.

Caproni et al., "Subacute cutaneous lupus erythematosus with pityriasis-like cutaneous manifestations," Int J Dermatol., 2001, 40(1):59-62.

Caricchio et al., "Ultraviolet B radiation-induced cell death: critical role of ultraviolet dose in inflammation and lupus autoantigen redistribution," The Journal of Immunology, 2003, 171:5778-5786.

Chen et al, "Advancing understanding, diagnosis, and therapies for cutaneous lupus erythematosus within the broader context of systemic lupus erythematosus," F1000Res., 2019, 8(F1000 Faculty Rev):332.

Chong et al., "Determining risk factors for developing systemic lupus erythematosus in patients with discoid lupus erythematosus," Br J Dermatol., 2012, 166(1):29-35.

Concha et al., "Advances in Cutaneous Lupus Erythematosus and Dermatomyositis: A report from the 4th International Conference on Cutaneous Lupus Erythematosus An ongoing need for international consensus and collaborations," J Invest Dermatol., Feb. 2019, 139(2):270-276.

Crowson & Magro, "The cutaneous pathology of lupus erythematosus: a review," J Cutan Pathol., 2001, 28(1):1-23.

(56) References Cited

OTHER PUBLICATIONS

Fabbri et al., "Cutaneous lupus erythematosus: diagnosis and management," Am J Clin Dermatol., 2003, 4(7):449-465.
Fonesca, et al., "Interleukin-6 as a key player in systemic inflammation and joint destruction," Autoimmunity Reviews, 2009, 8:538-542.
Forster et al., "Selective JAK3 Inhibitors with a Covalent Reversible Binding Mode Targeting a New Induced Fit Binding Pocket," Cell Chem Biol., 2016, 23:1335-1340.
Furie et al., "Anifrolumab, an Anti-Interferon-α Receptor Monoclonal Antibody, in Moderate-to-Severe Systemic Lupus Erythematosus," Arthritis & Rheumatology, 2017, 69:376-386.
Furie et al., "SAT0222 BIIB059, a monoclonal antibody targeting BDCA2, shows evidence of biological activity and early clinical proof of concept in subjects with active cutaneous le," Ann Rheum Dis., 2017, 76(Suppl 2):857.
Grieves et al., "Exonuclease TREX1 degrades double-stranded DNA to prevent spontaneous lupus-like inflammatory disease," Proc Natl Acad Sci USA., 2015, 112:5117-5122.
Gunther et al., "Familial chilblain lupus–a monogenic form of cutaneous lupus erythematosus due to a heterozygous mutation in TREX1," Dermatology (Basel), 2009, 219:162-166.
Gunther et al., "Systemic involvement in TREX1-associated familial chilblain lupus," J Am Acad Dermatol., 2013, 69:e179-81.
Guschin et al., "A major role for the protein tyrosine kinase JAK1 in the JAK/STAT signal transduction pathway in response to interleukin-6," Embo J., 1995, 14:1421-1429.
Hedrich et al., "Chilblain lupus erythematosus—a review of literature," Clin Rheumatol., 2008, 27(8):949-954.
Hornung et al., "More on remission of recalcitrant dermatomyositis treated with ruxolitinib," N Engl J Med., 2015, 372:1274.
Hornung et al., "Remission of recalcitrant dermatomyositis treated with ruxolitinib," N Engl J Med., 2014, 371:2537-2538.
Howell et al., "JAK/STAT inhibitors and other small molecule cytokine antagonists for the treatment of allergic disease," Ann Allergy Asthma Immunol., 2018, 120:367-375.
International Preliminary Report on Patentability for PCT/US2019/056533 dated Apr. 19, 2022, 8 pages.
Kalunian et al., "A Phase II study of the efficacy and safety of rontalizumab (rhuMAb interferon-α) in patients with systemic lupus erythematosus (ROSE)," Ann Rheum Dis., 2016, 75:196-202.
Katayama et al, "Delineating the healthy human skin UV response and early induction of interferon pathway in cutaneous lupus erythematosus," J Invest Dermatol., 2019, 139(9):2058-2061.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Khamashta et al., "Sifalimumab, an anti-interferon-α monoclonal antibody, in moderate to severe systemic lupus erythematosus: a randomised, double-blind, placebo-controlled study," Ann Rheumat Dis., 2016, 75:1909-1916.
Klaeschen et al, "JAK inhibitor ruxolitinib inhibits the expression of cytokines characteristic of cutaneous lupus erythematosus," Exp Dermatol., 2017, 26:728-730.
Klein et al., "Development of the CLASI as a tool to measure disease severity and responsiveness to therapy in cutaneous lupus erythematosus," Arch Dermatol., 2011, 147:203-208.
Konig et al, "Familial chilblain lupus due to a gain-of-function mutation in STING," Ann Rheum Dis., 2017, 76:468-472.
Kuhn & Landmann, "The classification and diagnosis of cutaneous lupus erythematosus," J Autoimmun., 2014, 48-49:14-19.
Kuhn et al., "Accumulation of apoptotic cells in the epidermis of patients with cutaneous lupus erythematosus after ultraviolet irradiation," Arthritis Rheum., 2006, 54:939-950.
Kuhn et al., "Lupus erythematosus revisited," Semin Immunopathol., 2016, 38:97-112.
Kunz et al., "Genome-wide association study identifies new susceptibility loci for cutaneous lupus erythematosus," Exp Dermatol., 2015, 24:510-515.
Lauffer et al., "Type I Immune Response Induces Keratinocyte Necroptosis and Is Associated with Interface Dermatitis," J Invest Dermatol., 2018, 138:1785-1794.
Mahajan et al, "Clearance Deficiency and Cell Death Pathways: A Model for the Pathogenesis of SLE," Front Immunol., 2016, 7:35.
Meller et al., "Ultraviolet radiation-induced injury, chemokines, and leukocyte recruitment: An amplification cycle triggering cutaneous lupus erythematosus," Arthritis Rheum., 2005, 52:1504-1516.
Merrill et al., "Safety profile and clinical activity of sifalimumab, a fully human anti-interferon α monoclonal antibody, in systemic lupus erythematosus: a phase I, multicentre, double-blind randomised study," Ann Rheum Dis., 2011, 70:1905-1913.
Mikita et al., "Recent advances in cytokines in cutaneous and systemic lupus erythematosus," J Dermatol., 2011, 38:839-849.
Morgan et al., "A role for JAK2 mutations in myeloproliferative diseases," Annu Rev Med., 2008, 59:213-222.
Mustelin et al., "Sources of pathogenic nucleic acids in systemic lupus erythematosus," Front Immunol., 2019, 10:238.
Ogunsanya et al., "Understanding the disease burden and unmet needs among patients with cutaneous lupus erythematosus: A qualitative study," Int J Womens Dermatol., 2018, 4:152-158.
Pardanani et al., "JAK2 inhibitor therapy in myeloproliferative disorders: rationale, preclinical studies and ongoing clinical trials," Leukemia, 2008, 22:23-30.
Park et al., "Homogeneous proximity tyrosine kinase assays: scintillation proximity assay versus homogeneous time-resolved fluorescence," Analytical Biochemistry, 1999, 269:94-104.
Peschke et al., "Deregulated type I IFN response in TREX1-associated familial chilblain lupus," J Invest Dermatol., 2014, 134:1456-1459.
Presto et al., "Computerized planimetry to assess clinical responsiveness in a phase II randomized trial of topical R333 for discoid lupus erythematosus," Br J Dermatol., 2018, 178:1308-1314.
Ravin, "Performulation," Remington's Pharmaceutical Sciences, 17th ed., Mack Publishing Company, Easton, Pa., 1985, p. 1418.
Ronnblom et al., "Autoimmune phenomena in patients with malignant carcinoid tumors during interferon-alpha treatment," Acta Oneal., 1991, 30:537-540.
Rothfield et al., "Lupus erythematosus: systemic and cutaneous manifestations," Clin Dermatol., Sep.-Oct. 2006, 24(5):348-362.
Saadeh et al., "Update on the role of plasmacytoid dendritic cells in inflammatory/autoimmune skin diseases," Exp Dermatol., 2016, 25:415-421.
Samotij et al., "Disease severity and prophylactic measures in patients with cutaneous lupus erythematosus: results of a worldwide questionnaire-based study," Postepy Dermatol Alergol., 2018, 35:192-198.
Santos & Verstovsek, "Efficacy of ruxolitinib for myelofibrosis," Expert Opin Pharmacother., 2014, 15:1465-1473.
Sarkar et al., "Photosensitivity and type I IFN responses in cutaneous lupus are driven by epidermal-derived interferon kappa," Ann Rheum Dis., 2018, 77:1653-1664.
Scholtissek et al., "Immunostimulatory Endogenous Nucleic Acids Drive the Lesional Inflammation in Cutaneous Lupus Erythematosus," J Invest Dermatol., 2017, 13(7):1484-1492.
Schwartz et al., "JAK inhibition as a therapeutic strategy for immune and inflammatory diseases," Nat Rev Drug Discov., 2017, 16:843-862.
Schwartz et al., "Type I/II cytokines, JAKs, and new strategies for treating autoimmune diseases," Nat Rev Rheumatol., 2016, 12:25-36.
Shreberk-Hassidim et al., "Janus kinase inhibitors in dermatology: A systematic review," J Am Acad Dermatol., 2017, 76:745-753.e19.
Sinha & Dey-Rao, "Genomic Investigation of Lupus in the Skin," J Investig Dermatol Symp Proc., 2017, 18:S75-S80.
Smolen et al., "Effect of interleukin-6 receptor inhibition with tocilizumab in patients with rheumatoid arthritis (OPTION study): a double-blind, placebo-controlled, randomised trial," Lancet, 2008, 371:987-997.
Spoerl et al., "Activity of therapeutic JAK 1/2 blockade in graft-versus-host disease," Blood, 2014, 123:3832-3842.

(56) References Cited

OTHER PUBLICATIONS

Srivastava et al, "Tofacitinib Represses the Janus Kinase-Signal Transducer and Activators of Transcription Signalling Pathway in Keratinocytes," Acta Derm Venereal., 2018, 98:772-775.

Szczych et al., "Trigger factors of cutaneous lupus erythematosus: a review of current literature," Lupus, 2017, 26(8):791-807.

Tebbe & Orfanos, "Epidemiology and socioeconomic impact of skin disease in lupus erythematosus," Lupus, 1997, 6(2):96-104.

Van Vollenhoven et al., "Efficacy and safety of ustekinumab, an IL-12 and IL-23 inhibitor, in patients with active systemic lupus erythematosus: results of a multicentre, double-blind, phase 2, randomised, controlled study," The Lancet, 2018, 392:1330-1339.

Wallace et al., "Baricitinib for systemic lupus erythematosus: a double-blind, randomised, placebo-controlled, phase 2 trial," Lancet, 2018, 392(10143):222-231.

Walling & Sontheimer, "Cutaneous lupus erythematosus: issues in diagnosis and treatment," Am J Clin Dermatol., 2009, 10(6):365-381.

Welsch et al., "Targeting JAK/STAT signalling in inflammatory skin diseases with small molecule inhibitors," Eur J Immunol., 2017, 47:1096-1107.

Wenzel & Tilting, "An IFN-associated cytotoxic cellular immune response against viral, self-, or tumor antigens is a common pathogenetic feature in interface dermatitis," J Invest Dermatol., 2008, 128:2392-2402.

Wenzel et al, "JAK1/2 Inhibitor Ruxolitinib Controls a Case of Chilblain Lupus Erythematosus," J Invest Dermatol., 2016, 136:1281-1283.

Wenzel et al, "The expression pattern of interferon-inducible proteins reflects the characteristic histological distribution of infiltrating immune cells in different cutaneous lupus erythematosus subsets," Br J Dermatol., 2007, 157:752-757.

Wenzel et al., "CXCR3 <-> ligand-mediated skin inflammation in cutaneous lichenoid graft-versus-host disease," J Am Acad Dermatol., 2008, 58:437-442.

Wenzel et al., "Enhanced type I interferon signalling promotes Th1-biased inflammation in cutaneous lupus erythematosus," J Pathol., 2005, 205:435-442.

Wenzel et al., "High expression of B lymphocyte stimulator in lesional keratinocytes of patients with cutaneous lupus erythematosus," Exp Dermatol., 2018, 27:95-97.

Wenzel et al., "Type I interferon-associated cytotoxic inflammation in cutaneous lupus erythematosus," Arch Dermatol Res., 2009, 301(1):83-86.

Werth & Merrill, "A double-blind, randomized, placebo-controlled, phase II trial of baricitinib for systemic lupus erythematosus: how to optimize lupus trials to examine effects on cutaneous lupus erythematosus," Br J Dermatol., 2019, 180(5):964-965.

Wollenberg et al, "Plasmacytoid dendritic cells: a new cutaneous dendritic cell subset with distinct role in inflammatory skin diseases," J Invest Dermatol., 2002, 119:1096-1102.

Xu et al., "Design, synthesis and biological evaluation of deuterated nintedanib for improving pharmacokinetic properties," J Label Compd Radiopharm., 2015, 58(7):308-312.

Yu et al., "Immunologic and genetic considerations of cutaneous lupus erythematosus: a comprehensive review," J Autoimmun. 2013, 41:34-45.

Zahn et al, "Interferon-α stimulates TRAIL expression in human keratinocytes and peripheral blood mononuclear cells: implications for the pathogenesis of cutaneous lupus erythematosus," Br J Dermatol., 2011, 165:1118-1123.

Zimmerman et al., "Assessment of Clinical Response to Janus Kinase Inhibition in Patients With Familial Chilblain Lupus and TREX1 Mutation," JAMA Dermatol., 2019, 155(3):342-346.

Sandborn et al., "Tofacitinib as Induction and Maintenance Therapy for Ulcerative Colitis," N. Engl. J. Med., May 2017, 376(18):1723-1736.

Chan et al., "Ruxolitinib Attenuates Cutaneous Lupus Development in a Mouse Lupus Model," Journal of Investigative Dermatology, 2015, 135(7):1912-1915.

ClinicalTrials.gov, "Open-label Study of Tofacitinib for Moderate to Severe Skin Involvement in Young Adults With Lupus," NCT03288324, dated Jul. 22, 2019, retrieved on Dec. 15, 2023, retrieved from URL<https://classic.clinicaltrials.gov/ct2/history/NCT03288324?V_6=View>, 10 pages.

ClinicalTrials.gov, "Safety and Efficacy of Filgotinib and Lanraplenib in Female With Moderately-to-Severely Active Cutaneous Lupus Erythematosus (CLE)," NCT03134222, dated Feb. 20, 2019, retrieved on Dec. 15, 2023, retrieved from URL<https://classic.clinicaltrials.gov/ct2/history/NCT03134222?V_32=View>, 9 pages.

Fetter et al., "AB0042 Preclinical Evaluation of JAK1 Selective Inhibitors INCB039110 and INCB054707 as Targeted Therapy of Cutaneous Lupus Erythematosus," Annals of the Rheumatic Diseases, May 27, 2019, 78(2): 1487.

Japanese Office Action in Japanese Application No. 2022-523053, dated Oct. 3, 2023, 16 pages (with English Translation).

Meller et al., "Chemokines in the Pathogenesis of Lichenoid Tissue Reactions," Journal of Investigative Dermatology, 2009, 129(2):315-319.

Okiyama, "Mucocutaneous diseases and murine models with death of keratinocytes induced by lichenoid tissue reaction/interface dermatitis," Japanese Journal of Clinical Immunology, Jan. 1, 2015, 38(1):1-7 (with English Abstract).

Szilveszter et al., "Tyrosine Kinases in Autoimmune and Inflammatory Skin Diseases," Frontiers in Immunology, Aug. 9, 2019, 10(1862):1-21.

Wenzel et al., "An IFN-Associated Cytotoxic Cellular Immune Response against Viral, Self-, or Tumor Antigens Is a Common Pathogenetic Feature in 'Interface Dermatitis,'" Journal of Investigative Dermatology, 2008, 128(10):2392-2402.

\* cited by examiner

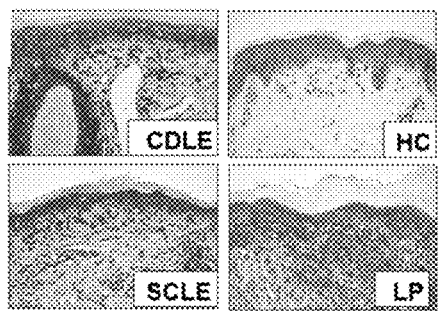
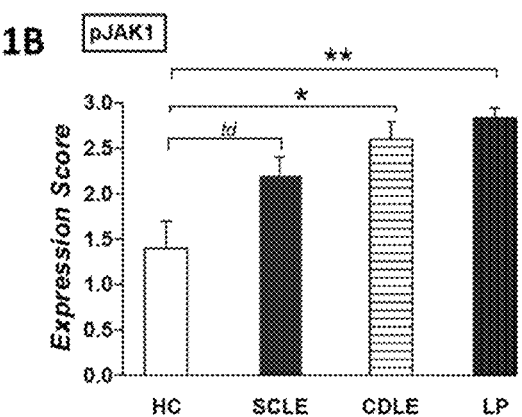
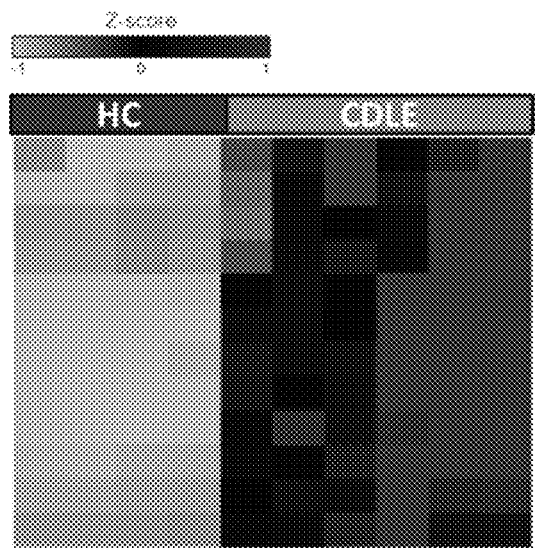
FIGs. 1A-1D

USE OF JAK1 INHIBITORS FOR THE TREATMENT OF CUTANEOUS LUPUS ERYTHEMATOSUS AND LICHEN PLANUS (LP)

TECHNICAL FIELD

The present application provides methods for the treatment of cutaneous lupus erythematosus and/or Lichen planus (LP) using compounds that modulate the activity of Janus kinase (JAK) 1.

BACKGROUND

Cutaneous lupus erythematosus (CLE) is an inflammatory autoimmune skin disease with heterogenic subtypes varying from localized discoid plaques to severe and widespread erythrosquamous lesions in affected patients (see e.g., Kuhn & Landmann, *J. Autoimmun.* 2014, 48-49:14-19). The disease is characterized by a typical histological pattern called "interface dermatitis" (ID) consisting of colloid bodies and an anti-epidermal cytotoxic lymphocytic infiltrate in the dermoepidermal junction which is orchestrated by IFN-regulated proinflammatory cytokines (see e.g., Wenzel & Tüting, *J. Invest. Dermatol.* 2008, 128:2392-2402; and Wenzel et al, *Br. J. Dermatol.* 2007, 157:752-757).

CLE is of multifactorial origin; including both genetic and environmental risk factors (see e.g., Kunz et al, *Exp. Dermatol.* 2015, 24:510-515; Sinha & Dey-Rao, *J. Investig. Dermatol. Symp. Proc.,* 2017, 18:S75-S80; and Szczech et al, *Lupus,* 2017, 26:791-807). In particular UV radiation promotes cellular damage, apoptosis and release of DNA-containing blebs. It is considered that cell debris clearance is impaired entailing secondary necrosis (see e.g., Kuhn et al, *Arthritis Rheum.* 2006, 54:939-950; Caricchio et al, *The Journal of Immunology* 2003, 171:5778-5786; and Mahajan et al, *Front Immunol.* 2016, 7). In some cases such as familial chilblain lupus the underlying cause can be TREX1 gene mutations leading to a dysfunctional TREX1 exonuclease and high accumulation of cytosolic DNA (see e.g., Günther et al, *J. Am. Acad. Dermatol.* 2013, 69:e179-81; Grieves et al, *Proc. Natl. Acad Sci. U.S.A.* 2015, 112:5117-5122; Günther et al, *Dermatology (Basel),* 2009, 219:162-166; and Peschke et al, *J. Invest. Dermatol.* 2014, 134:1456-1459).

When nuclear components, such as endogenous nucleic acid motifs, are released out of the nucleus due to cellular damage, they can be perceived as danger associated molecular patterns (DAMPs) (see e.g., Scholtissek et al, *J. Invest. Dermatol.* 2017, 137:1484-1492). There is evidence that keratinocytes and particularly plasmacytoid dendritic cells (pDCs) react on DAMPs inappropriately with immense type I IFN production through TLR-dependent or TLR-independent pathways in CLE (see e.g., Mustelin et al, *Front. Immunol.* 2019, 10:238; Wollenberg et al, *J. Invest. Dermatol.* 2002, 119:1096-1102; Wenzel et al, *Arch. Dermatol. Res.* 2009, 301:83-86; Yu et al, *J. Autoimmun.* 2013, 41:34-45; and Katayama et al, *J. Invest. Dermatol.* DOI: 10.1016/j.jid.2019.02.035). Undergoing an autocrine loop IFNs bind to IFN-α/β receptors on keratinocytes, thus activating JAK/STAT pathway and expression of proinflammatory mediators such as CXCL10. It is known that CXCL10 recruits CXCR3+ effector cells and pDCs into skin lesions (see e.g., Wenzel et al, *Arch. Dermatol. Res.* 2009, 301:83-86; and Wenzel et al, *J. Pathol.* 2005, 205:435-442). Those effector cells induce keratinocytic necroptosis (see e.g., Lauffer et al, *J. Invest. Dermatol.* 2018, 138:1785-1794), cytokine release and a continuous "self-recruitment" as a hallmark of chronic inflammation (see e.g., Meller et al, *Arthritis Rheum.* 2005, 52:1504-1516).

This circle can result in a strong burden for quality of life (see e.g., Samotij et al, *Postepy Dermatol. Alergol.* 2018, 35:192-198; and Ogunsanya et al, *Int. J. Womens Dermatol.* 2018, 4:152-158). Following current guidelines, corticosteroids and antimalarials are established as first-line treatment of CLE. However, corticosteroids are limited by side effects and long-term treatment, particularly in antimalarial-resistant patients, can be challenging. In addition, no specifically approved drugs exist for CLE and only a few clinical trials have been conducted, not least because of clinical heterogeneity and thus challenging trial design (see e.g., Chen et al, *F1000Res.* 2019, 8).

The American College of Rheumatology (ACR) has established a scheme of eleven clinical and lab criteria for the purpose of distinguishing Systemic Lupus Erythematosus (SLE) from other autoimmune diseases. The ACR guidelines require four of eleven criteria to be met for a diagnosis of SLE, however, only four of the criteria are cutaneous in nature (malar rash, discoid lesions, mucosal ulcers, and photosensitivity) and therefore involvement of skin pathologies is not obligatory for the diagnosis of SLE. Conversely, cutaneous lupus erythematosus (CLE) subtypes can occur in the absence of systemic disease (SLE); CLE is two to three times more frequent than SLE (see e.g., Tebbe & Orfanos, *Lupus,* 1997, 6(2):96-104).

Considering these limitations, there is a medical need for new therapeutic options. This application is directed to that need and others.

SUMMARY

The present application provides methods of treating a disease selected from cutaneous lupus erythematosus (CLE) and Lichen planus (LP) in a patient in need thereof, comprising administering to the patient a therapeutically effective amount of a JAK1 selective inhibitor provided herein.

DESCRIPTION OF DRAWINGS

FIGS. 1A-1D show the functional role of JAK1 expression in CLE skin lesions. FIG. 1A shows representative immunohistochemical sections (anti-phosphoJAK1 staining) from skin samples of patients with different inflammatory skin disorders (subacute cutaneous lupus erythematosus (SCLE, n=5), chronic discoid lupus erythematosus (CDLE, n=5), Lichen planus (LP, n=6) and healthy controls (HC, n=5)), original magnification ×200. FIG. 1B shows the expression of pJAK1, scored semiquantitatively by scoring from 0 ≙ no expression to 3 ≙ strong expression (see e.g., Wenzel et al. *J. Pathol.* 2005, 205:435-442). All bars show mean±SEM td ≙ p<0.1,* ≙ p<0.05, ** ≙ p<0.01 (Kruskal-Wallis-Test). FIG. 1C shows upregulated expression of IFN-associated genes in CLE lesional skin (2-fold, p<0.01; Welch's t-test) compared to healthy controls (HC). FIG. 1D shows KEGG pathways upregulated in CLE. KEGG pathway classification was performed using Database for Annotation, Visualization and Integrated Discovery (DAVID ver. 6.8). P-values were generated with EASE Score. Count: number of genes >2-fold upregulated in CLE within the respective KEGG pathway.

FIG. 2A shows mean area intensity in pixel values of anti-pJAK1- antibody staining in stimulated HaCaT (eNA), stimulated and inhibitor-treated HaCaT (eNA+ JAK1 inhibitor {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile (i.e., INCB039110); eNA+JAK1/2, inhibitor:ruxolitinib) and unstimulated HaCaT (C-Medium). Measurement was performed out using Fiji software. Measurements per entity: n=5. All scatter dot plots show mean+SEM,  ≙ p<0.01 (Mann-Whitney U test). FIG. 2B shows representative immunofluorescence micrographs of eNA-stimulated untreated (eNA) or inhibitor-treated (eNA+JAK1, inhibitor:INCB039110; eNA+JAK1/2, inhibitor:ruxolitinib) HaCaT as well as unstimulated HaCaT-cells (Medium Control). Anti-pJAK1 antibody staining in red, DAPI staining of the nucleus in blue, original magnification ×400. FIG. 2C shows expression of CLE-typical genes within eNA-stimulated NHEK (+, 4 samples) and >2-fold downregulated expression (p<0.05; Welch's t-test) after treatment of stimulated NHEK with JAK1 selective INCB039110 (JAK1; 4 samples). FIG. 2D shows the effect of different JAK inhibitors on CXCL10 expression in stimulated HaCaT after 24 hours of incubation. Cells were treated with JAK1 selective INCB039110 (JAK1), JAK1/2 selective Ruxolitinib (JAK1/2) and JAK3 selective FM-381 (JAK3). Measured by ELISA. All bars show mean+SEM, * ≙ p<0.001, ** ≙ p<0.01, td ≙ p<0.1 (Mann-Whitney U test). FIG. 2E shows micrographs representing the expression of CXCL10 in stimulated cells (eNA, n=3) and JAK1 inhibitor treated cells (INCB039110) after stimulation (eNA+JAK1, n=3), original magnification ×400, with corresponding CXCL10 expression score. All bars show mean SEM, * ≙ p<0.05; (Mann-Whitney U test).

FIG. 3A shows clinical findings of UV-stimulated (started on day –3; 3×450 mJ/cm$^2$ for 115 seconds) TREX1$^{-/-}$ mice (n=8) on baseline (day 0, start of treatment) and after 4 and 7 days of treatment with JAK1 selective INCB039110 or placebo. FIG. 3B shows mean score of the mouse-adapted revised CLE-disease-area-and-severity index (Mouse RCLASI) ±SEM in n=4 mice per group. FIG. 3C shows histological (H&E) and immunohistological (CD45) micrographs of lesional skin, original magnification ×400. Corresponding inflammation score of CD45 expression in lesional skin of placebo-treated and JAK1-inhibitor treated mice. All bars show mean±SEM, ** ≙ p<0.01 (Mann-Whitney U test).

FIG. 4A shows the effect of JAK1 selective INCB054707 (n=15) or placebo control (n=30) treatment on the incidence of spontaneous skin lesions when daily dosing was initiated from 11 weeks of age onwards (signified by an arrow). FIG. 4B shows mean daily cutaneous skin lesion score. FIG. 4C shows the cumulative skin lesion disease burden (area under the curve) following of JAK1 selective INCB054707 (n=15) or placebo control (n=30) daily treatment. In a second, independent, experiment using the lupus-prone MRL-lpr mouse model, FIG. 4D shows the dose-dependent effect of JAK1 selective INCB054707 (n=15 per group) on daily cutaneous skin lesion score. FIG. 4E shows the cumulative skin lesion disease burden (area under the curve) is dose-dependently reduced following JAK1 selective INCB054707 (n=15 per group) compared to placebo control (n=15) treated MRL-lpr mice. All bars show mean+SEM, * ≙ p<0.001 and ** ≙ <0.0001 (Mann-Whitney Utest or Kruskal-Wallis test). Incidence of skin lesions calculated with Kaplan-Meier Log-rank test.

FIG. 5A-C shows the dose-dependent effect of JAK1 selective INCB054707 (n=6 per group) or placebo control (n=6) treatment resulting in downregulation of multiple inflammatory markers.

DETAILED DESCRIPTION

Figure 2A:
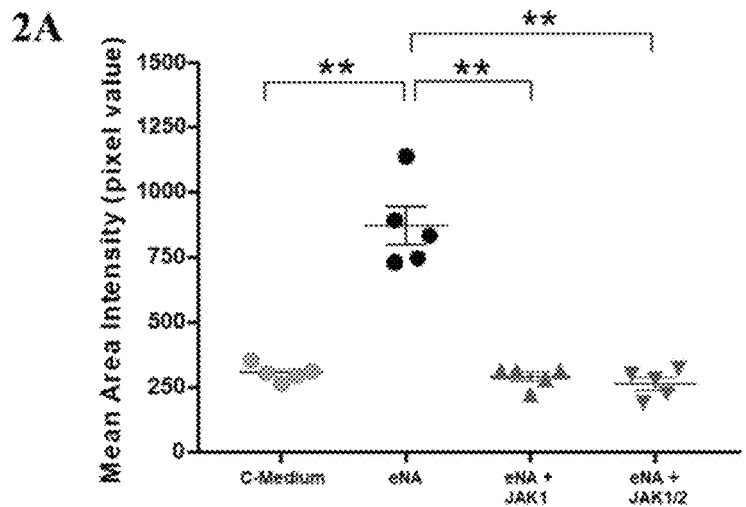
FIGS. 2A-2E show the effects of pharmacological JAK1 inhibition on proinflammatory cytokine expression and IFN-associated gene regulation in cultured keratinocytes.

The present application provides, inter alia, methods of treating a disease selected from cutaneous lupus erythematosus (CLE) and Lichen planus (LP) in a patient in need thereof, comprising administering a therapeutically effective amount of JAK1 selective inhibitor, or a pharmaceutically acceptable salt thereof. In some embodiments, the disease is cutaneous lupus erythematosus (CLE). In some embodiments, the cutaneous lupus erythematosus (CLE) is selected from acute cutaneous lupus erythematosus, subacute cutaneous lupus erythematosus, and chronic cutaneous lupus erythematosus. In some embodiments, the cutaneous lupus erythematosus (CLE) is acute cutaneous lupus erythematosus. In some embodiments, the cutaneous lupus erythematosus is selected from subacute cutaneous lupus erythematosus (SCLE) and chronic discoid lupus erythematosus (CDLE). In some embodiments, the cutaneous lupus erythematosus is subacute cutaneous lupus erythematosus (SCLE). In some embodiments, the cutaneous lupus erythematosus is chronic discoid lupus erythematosus (CDLE). In some embodiments, the disease is Lichen planus (LP).

As used herein, "cutaneous lupus" refers to a form of the disease in which symptoms are restricted to those that affect the skin. For example, a patient may be diagnosed with cutaneous lupus, but that does not mean that he or she has SLE, which affects multiple parts of the body. Similarly, if a patient has SLE, it does not mean that he or she will necessarily have cutaneous lupus. Accordingly the Cutaneous Lupus Area and Severity Index (CLASI) scoring system was devised, which quantitatively measures disease activity and damage (see e.g., Albrecht et al., *J. Invest. Dermatol.* 2005, November; 125(5):889-94). This index, which accounts for lesional morphology as well as anatomic location, has since been validated by reliability testing for both dermatologists and rheumatologists.

Cutaneous lupus is divided into several subtypes, including acute cutaneous lupus erythematosus, subacute cutaneous lupus erythematosus, and chronic cutaneous lupus erythematosus. Acute cutaneous LE typically presents in the third decade of life and is frequently associated with active SLE. The most typical form of acute cutaneous lupus is a malar rash-flattened areas of red skin on the face that resemble a sunburn (see e.g., Fabbri et al., *Am. J. Clin. Dermatol.* 2003, 4(7):449-65). These lesions are typically transient, sun-induced, and non-scarring. Malar rashes have been reported to be present in ~50% of SLE patients at the time of diagnosis, with clinical activity of the rash paralleling that of the systemic disease (see e.g., Rothfield et al., *Clin. Dermatol.*; 2006, September-October; 24(5):348-62).

Chronic cutaneous lupus includes discoid LE (DLE), LE profundus (LEP), chilblain LE (CHLE), and LE tumidus (LET). In some embodiments, the chronic cutaneous lupus is selected from discoid lupus erythematosus (DLE), lupus erythematosus profundus (LEP), chilblain lupus erythematosus (CHLE), and lupus erythematosus tumidus (LET).

Discoid LE lesions are the most common lesions of Chronic cutaneous lupus erythematosus (CCLE) and appear as disk-shaped, round lesions. DLE occurs more frequently in women in their fourth and fifth decade of life. Patients with DLE generally have a more benign disease course as compared to patients with other CLE subtypes, with only most patients (~90-95%) never develop lupus in other organ systems (SLE) symptoms (see e.g., Crowson & Magro, *J. Cutan. Pathol.* 2001, 28(1):1-23; and Chong et al., *Br. J. Dermatol.* 2012, 166(1):29-35). The sores usually appear on the scalp and face but sometimes they will occur on other parts of the body as well. Discoid lupus lesions are often red, scaly, and thick. Usually, the lesions do not hurt or itch. Histologic examination of active DLE lesion reveals hyperkeratosis, dilated compact keratin-filled follicles, vacuolar degeneration of the basal keratinocytes, and an intensely inflammatory dermal infiltrate.

LE profundus (LEP), or panniculitis, features painful firm subcutaneous nodules occurring in areas of increased fat deposition, such as the upper arms and legs, face, and breasts. LEP tends to have a chronic course, characterized by remission and flares, and ultimately leaving atrophic scars (see e.g., Fabbri et al., *Am. J. Clin. Dermatol.* 2003, 4(7): 449-65). Histology shows lobular panniculitis with a dense lymphocytic infiltrate.

Chilblain lupus (CHLE) is a rare form of CCLE resembling frostbite. Lesions appear as painful, violaceous plaques and nodules in cold-exposed areas. Central erosions or ulcerations may occur on acral surfaces, such as fingers, toes, heels, nose, and ears. Chilblain lupus occurs when there is a temperature drop, and can be difficult to distinguish from frostbite. Pathology shows epidermal atrophy, interface vacuolization, and a perivascular mononuclear infiltrate. Approximately 80% of patients with CHLE will not develop SLE (see e.g., Hedrich et al., *Clin. Rheumatol.* 2008, 27(8):949-54).

Lupus tumidus is a subtype of CCLE characterized by extreme photosensitivity and a benign course occurring preferentially in men, unlike SLE which primarily occurs in women. Clinically, these lesions appear on the face as erythematous, edematous, urticaria-like polycyclic plaques with sharp raised borders and smooth surfaces.

Primarily in young to middle aged women, subacute cutaneous lupus (SCLE) lesions are described as having a scaly red annular ("ring-like") redness with central clearing. The lesions may also be polycyclic—that is, having the appearance of multiple rings coming together. There are two morphologic variants of SCLE: annular and papulosquamous. The annular variant is characterized by scaly annular erythematous plaques, which tend to coalesce and produce a polycyclic array (see e.g., Walling & Sontheimer, *Am. J. Clin. Dermatol.* 2009, 10(6):365-81). The papulosquamous variant can resemble eczema, as well as pityriasis in some instances (see e.g., Caproni et al. *Int. J. Dermatol.* 2001, 40(1):59-62). SCLE lesions occur in sun-exposed areas, including the upper thorax ('V' distribution), upper back, and the extensor surfaces of arms and forearms. About 10% of SLE patients will have SCLE lesions and those patients with systemic disease tend to have only mild symptoms in other organ compartments. Pathologic examination of SCLE lesions demonstrates hydropic degeneration of the basal keratinocytes, dermal edema, hyperkeratosis, follicular plugging, and a sparse superficial inflammatory infiltrate (see e.g., Fabbri et al., *Am. J. Clin. Dermatol.* 2003, 4(7): 449-65).

First evidence for a functional role of type I IFNs in lupus erythematosus (i.e., LE) came from clinical observations in patients suffering from carcinoid tumors which were treated with recombinant IFNα and developed SLE due to this therapy (see e.g., Ronnblom et al, *Acta Oncol.* 1991, 30:537-540). This was supported by findings in multiple sclerosis patients who developed CLE-like lesions at the injection side of recombinant IFNβ after subcutaneous application (see e.g., Arrue et al, *J. Cutan. Pathol.* 2007, 34, Suppl 1:18-21). Gene expression analyses in both SLE and CLE revealed a strong expression of type I IFN associated proinflammatory cytokines in blood and skin in association with disease activity (see e.g., Kuhn et al, *Semin. Immunopathol.* 2016, 38:97-112; and Mikita et al, *J. Dermatol.* 2011, 38:839-849). These findings are supported by the data described herein, which demonstrates a strong expression of IFN-regulated genes and immune pathways within CLE skin lesions (see e.g., FIGS. 1A-1D).

Previous reports describing strong IFN-signatures prompted the development of anti-IFN directed therapeutic strategies of LE patients. Anti-IFNα-agents (e.g., sifalimumab, rontalizumab) were the first drugs tested in clinical studies. These agents reduced the IFN signature in the blood but had limited effect on disease activity. Without being bound by theory, this was possibly due to the high variability of the different type I IFNs, including not only IFNα but also IFNβ and IFNκ binding to the same receptors (see e.g., Kalunian et al, *Ann. Rheum. Dis.* 2016, 75:196-202; Merrill et al, *Ann. Rheum. Dis.* 2011, 70:1905-1913; and Sarkar et al, *Ann. Rheum. Dis.* 2018, 77:1653-1664). Accordingly, targeting the common receptor was more effective: the anti-IFNαβ-receptor antibody anifrolumab significantly reduced the CLASI skin score in SLE patients in a recent clinical study (see e.g., Furie et al, *Arthritis & Rheumatology,* 2017, 69:376-386). Alternative strategies focused on "indirect" inhibition of the IFN system by (i) targeting the IFN-producing cells or (ii) the intracellular IFN-pathway. In skin and blood plasmacytoid DCs are regarded as the main IFN-producing cells (see e.g., Saadeh et al, *Exp. Dermatol.* 2016, 25:415-421) and the pDC-specific antibodies BIIB059 and VIB7734 are now in clinical trials with first results indicating a decline of the CLASI-activity score (see e.g., Furie et al, *Ann. Rheum. Dis.* 2017, 76 (Suppl 2):857).

The JAK family consists of four non-receptor tyrosine kinases (JAK1-3, TYK2) that transduce signals from growth factors and cytokines such as type I/III IFNs. JAK inhibitors were initially developed for the treatment of haematologic diseases with definite JAK-mutations showing anticlonal activity (see e.g., Morgan et al, *Annu. Rev. Med.* 2008, 59:213-222; and Pardanani et al, *Leukemia* 2008, 22:23-30), but they also provide significant immunosuppressive effects (see e.g., Santos & Verstovsek, *Expert Opin. Pharmacother.* 2014, 15:1465-1473; Schwartz et al, *Nat. Rev. Drug Discov.* 2017, 16:843-862; Schwartz et al, *Nat. Rev. Rheumatol.* 2016, 12:25-36; and Howell et al, *Ann. Allergy Asthma Immunol.* 2018, 120:367-375).

Earlier studies revealed activation of JAK/STAT pathway and JAK protein expression in CLE and associated skin disorders (see e.g., Scholtissek et al, *J. Invest. Dermatol.* 2017, 137:1484-1492; Alves de Medeiros et al, *PLoS ONE* 2016, 11:e0164080; and Wenzel et al, *J. Am. Acad. Dermatol.* 2008, 58:437-442)). JAK inhibitors provided beneficial effects in interface dermatitides including graft-versus-host disease (see e.g., Spoerl et al, *Blood,* 2014, 123:3832-3842), dermatomyositis (see e.g., Hornung et al, *N. Engl. J. Med.* 2014, 371:2537-2538; and Hornung et al, *N. Engl. J. Med.* 2015, 372:1274) and LE (see e.g., Wenzel et al, *J. Invest. Dermatol.* 2016, 136:1281-1283; and Briand et al, *Ann. Rheum. Dis.* 2019, 78:431-433) in addition to other inflammatory skin conditions (see e.g., Baneree et al, *Drugs,* 2017, 77:521-546; Welsch et al, *Eur. J. Immunol.* 2017, 47:1096-1107; and Shreberk-Hassidim et al, *J. Am. Acad. Dermatol.*

2017, 76:745-753.e19). In CLE, JAK1/2 inhibitors ruxolitinib (see e.g., Wenzel et al, *J. Invest. Dermatol.* 2016, 136:1281-1283; Briand et al, *Ann. Rheum. Dis.* 2019, 78:431-433; and Klaeschen et al, *Exp. Dermatol.* 2017, 26:728-730) and baricitinib (see e.g., Zimmerman et al, *JAMA Dermatol.* DOI: 10.1001/jamadermatol.2018.5077) as well as JAK1/3 inhibitor tofacitinib (see e.g., König et al, *Ann. Rheum. Dis.* 2017, 76:468-472) have been reported to be successful in patient's treatment, and these drugs significantly decrease the expression of CLE-typical chemokines in vitro (see e.g., Klaeschen et al, *Exp. Dermatol.* 2017, 26:728-730; and Srivastava et al, *Acta. Derm. Venereol.* 2018, 98:772-775). One potential disadvantage of these drugs are side effects, including anemia and thrombopenia, which may occur in some patients. The side effects are associated with JAK2 and JAK3 inhibition.

Notably, recent reports of a double-blind placebo-controlled trial for the treatment of SLE suggest that baricitinib was not effective compared to placebo (see e.g., Wallace et al, *Lancet,* 2018, 392(10143):222-231; and Werth & Merrill, *Br. J. Dermatol.* 2019, 180(5):964-965). Baricitinib (2 mg or 4 mg) was dosed once daily for 24 weeks. Eligible patients were aged 18 years or older, had a diagnosis of systemic lupus erythematosus (SLE), and had active disease involving skin or joints. The primary endpoint was the proportion of patients achieving resolution of arthritis or rash at week 24, as defined by Systemic Lupus Erythematosus Disease Activity Index-2000 (SLEDAI-2K).

In an exploratory end point, the Cutaneous Lupus Erythematosus Disease Area and Severity Index (CLASI) was evaluated, finding no improvement on the CLASI activity score with baricitinib. Unlike SLEDAI, the CLASI scoring system has been fully validated as a cutaneous-specific end point for SLE and successfully used in a number of phase II clinical trials for SLE and CLE. Recent reports also agree that the CLASI scoring system should be used as the skin outcome for lupus trials examining responsiveness in the skin (see e.g., Albrecht J, et al., *J. Invest. Dermatol.* 2005; 125:889-94; Klein et al., *Arch. Dermatol.* 2011, 147:203-8; Furie et al., *Arthritis Rheumatol.* 2017, 69:376-86; van Vollenhoven et al., *The Lancet* 2018, 392:1330-9; Khamashta et al., *Ann. Rheumat. Dis.* 2016, 75:1909-16; and Concha et al., *J. Invest. Dermatol.* 2018, https://doi.org/10.1016fj.jid.2018.08.017).

The methods provided herein utilize compounds or salts that are JAK1 inhibitors (e.g., JAK1 selective inhibitors). In some embodiments, the compound is selected from:

{1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile;

4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide;

[3-[4-(7H-pyrrolo[2,3-d]pyrimidin-4-yl)-1H-pyrazol-1-yl]-1-(1-[2-(trifluoromethyl)pyrimidin-4-yl]carbonyl)piperidin-4-yl)azetidin-3-yl]acetonitrile;

4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide;

((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile;

3-[1-(6-chloropyridin-2-yl)pyrrolidin-3-yl]-3-[4-(7H-pyrrolo[2,3-d]pyrimidin-4-yl)-1H-pyrazol-1-yl]propanenitrile;

3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile;

4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile;

4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile;

[trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile;

{trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile;

5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide;

4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide;

5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide;

{1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{trans-3-(4-{[4-(([(1S)-2-hydroxy-1-methylethyl]amino)methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile; and {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

or a pharmaceutically acceptable salt of any of the aforementioned.

In some embodiments, the compounds or salt is selective for JAK1 over JAK2, JAK3 and TYK2. For example, some of the compounds described herein, or a pharmaceutically acceptable salts thereof, preferentially inhibit JAK1 over one or more of JAK2, JAK3, and TYK2. JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (see e.g., Fonesca, et al., *Autoimmunity Reviews,* 8:538-42, 2009). Because IL-6 signals, at least in part, through JAK1, IL-6 can be indirectly through JAK1 inhibition, resulting in potential clinical benefit (see e.g., Guschin, et al. Embo J 14:1421, 1995; and Smolen, et al. *Lancet* 371:987, 2008). In other autoimmune diseases and cancers, elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases, as described herein.

In some embodiments, the compounds or salt inhibits JAK1 preferentially over JAK2 (e.g., having a JAK2/JAK1 IC$_{50}$ ratio >1). In some embodiments, the compounds or salts provided herein are about 10-fold more selective for JAK1 over JAK2. In some embodiments, the compounds or salts provided herein are about 3-fold, about 5-fold, about 10-fold, about 15-fold, or about 20-fold more selective for JAK1 over JAK2 as calculated by measuring IC$_{50}$ at 1 mM ATP (see Example 1).

In some embodiments, the JAK1 inhibitor is a compound of Table 1, or a pharmaceutically acceptable salt thereof. The compounds in Table 1 are JAK1 selective inhibitors (e.g., selective over JAK2, JAK3, and TYK2). The IC$_{50}$ values obtained by the method of Example 1 at 1 mM ATP are shown in Table 1.

TABLE 1

| Comp. No. | Prep. | Name | Structure | JAK1 IC$_{50}$ (nM) | JAK2/JAK1 |
|---|---|---|---|---|---|
| 1 | US 2011/0224190 (Example 1) | {1-{1-[3-Fluoro-2-(trifluoromethyl)isonicotinoyl]piperidin-4-yl}-3-[4-(7H-pyrrolo[2,3-c]pyrimidin-4-yl)-1H-pyrazol-1-yl]azetidin-3-yl}acetonitrile | 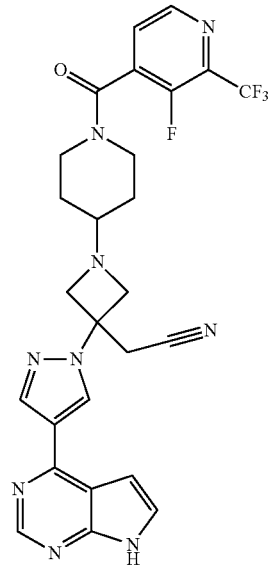 [SMILES: N#CCC1(n2cc(-c3ncnc4[nH]ccc34)cn2)CN(C2CCN(C(=O)c3ccnc(C(F)(F)F)c3F)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 2 | US 2011/ 0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 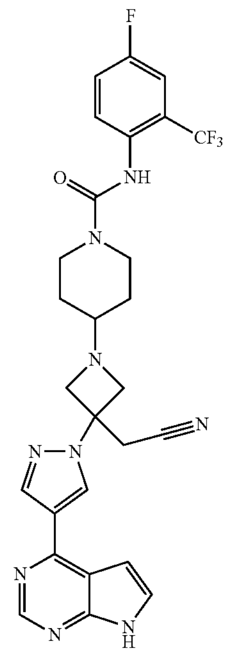 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |
| 3 | US 2011/ 0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 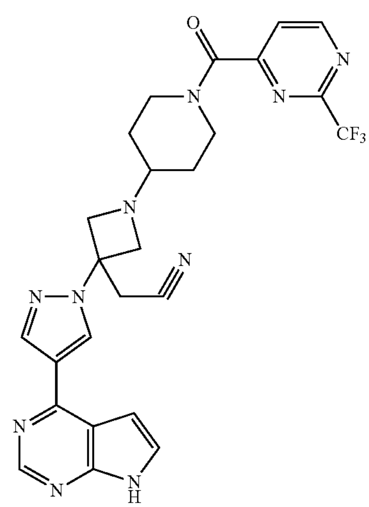 [SMILES: N#CCC1(n2cc(-c3ncnc4[nH]ccc34)cn2)CN(C2CCN(C(=O)c3ccnc(C(F)(F)F)n3)CC2)C1] | + | >10 |
| 4 | US 2014/ 0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 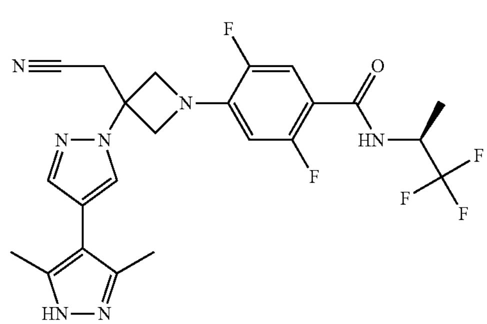 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |

TABLE 1-continued

| Comp. No. | Prep. | Name | Structure | JAK1 IC$_{50}$ (nM) | JAK2/ JAK1 |
|---|---|---|---|---|---|
| 5 | US 2014/ 0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 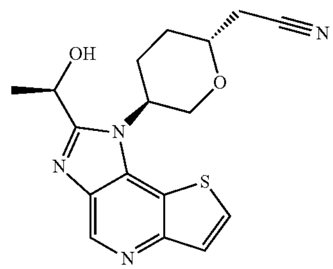 [SMILES: C[C@@H](O)c1nc2cnc3ccsc3c2n1[C@H]1CC[C@H](CC#N)OC1] | ++ | >10 |
| 6 | US 2010/ 0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 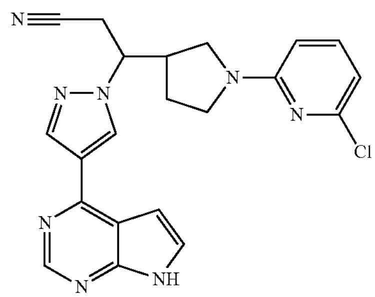 [SMILES: N#CCC(C1CCN(c2cccc(Cl)n2)C1)n1cc(-c2ncnc3[nH]ccc23)cn1] | + | >10 |
| 7 | US 2010/ 0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 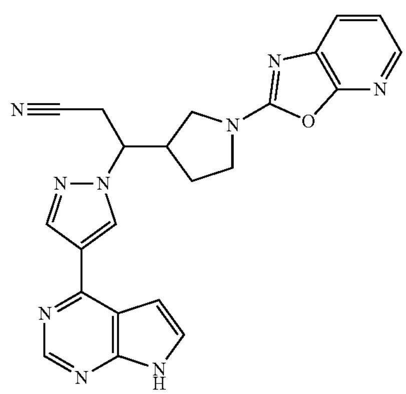 [SMILES: N#CCC(C1CCN(c2nc3cccnc3o2)C1)n1cc(-c2ncnc3[nH]ccc23)cn1] | + | >10 |
| 8 | US 2011/ 0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 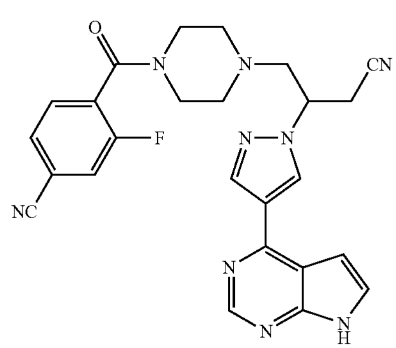 [SMILES: N#CCC(CN1CCN(C(=O)c2ccc(C#N)cc2F)CC1)n1cc(-c2ncnc3[nH]ccc23)cn1] | + | >10 |

TABLE 1-continued

| Comp. No. | Prep. | Name | Structure | JAK1 IC$_{50}$ (nM) | JAK2/ JAK1 |
|---|---|---|---|---|---|
| 9 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 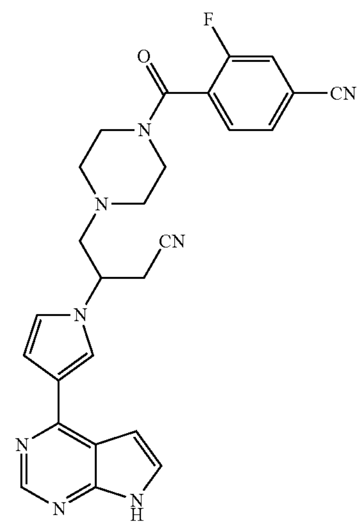 [SMILES: N#CCC(CN1CCN(C(=O)c2ccc(C#N)cc2F)CC1)n1ccc(-c2ncnc3[nH]ccc23)c1] | + | >10 |
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 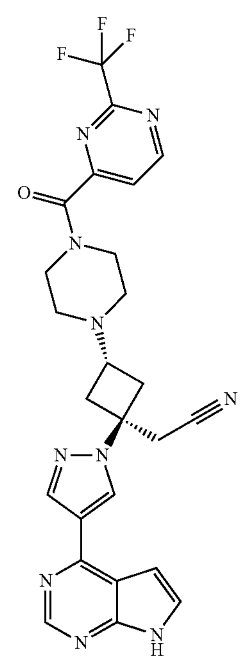 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 11 | US 2012/ 0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 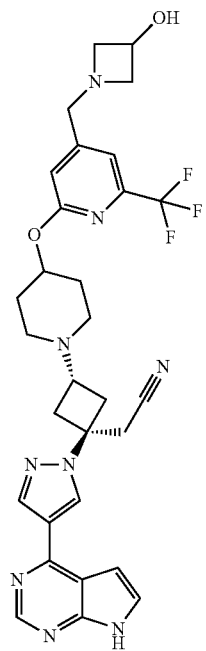 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |
| 12 | US 2012/ 0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 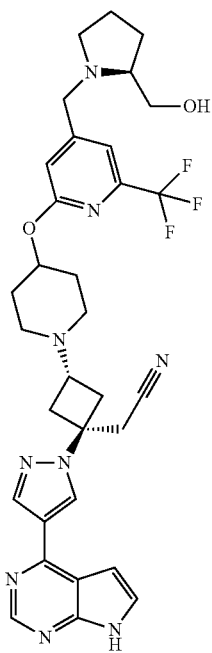 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 13 | US 2012/ 0149681 (Example 162) | {trans-3-(4-{[4-{[(2R)-2-(hydroxymethyl)pyrroli-din-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 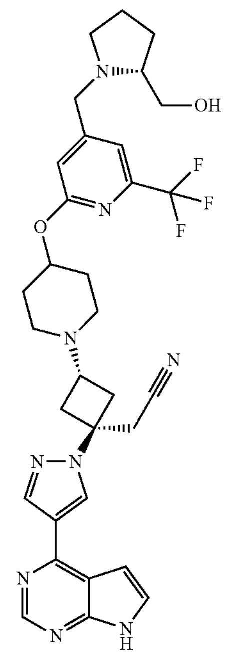 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |
| 14 | US 2012/ 0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 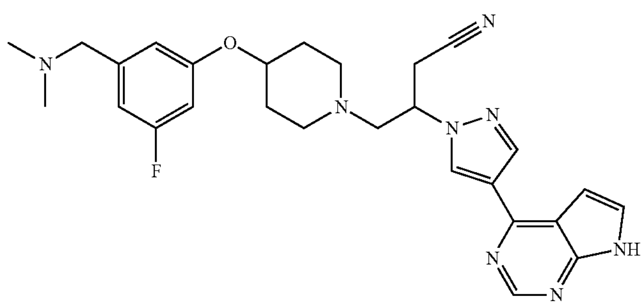 [SMILES: CN(C)Cc1cc(F)cc(OC2CCN(CC(CC#N)n3cc(-c4ncnc5[nH]ccc45)cn3)CC2)c1] | + | >10 |
| 15 | US 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 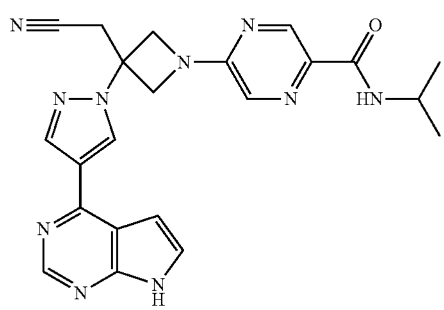 [SMILES: CC(C)NC(=O)c1cnc(N2CC(CC#N)(n3cc(-c4ncnc5[nH]ccc45)cn3)C2)cn1] | + | >10 |

TABLE 1-continued

| Comp. No. | Prep. | Name | Structure | JAK1 IC$_{50}$ (nM) | JAK2/ JAK1 |
|---|---|---|---|---|---|
| 16 | US 2013/ 0018034 (Example 28) | 4-{3-(cyanomethyl)-3- [4-(7H-pyrrolo[2,3- d]pyrimidin-4-yl)-1H- pyrazol-1-yl]azetidin-1- yl}-2,5-difluoro-N- [(1S)-2,2,2-trifluoro-1- methylethyl]benzamide | 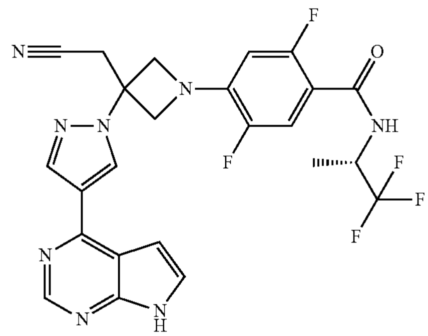 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/ 0018034 (Example 34) | 5-{3-(cyanomethyl)-3- [4-(1H-pyrrolo[2,3- b]pyridin-4-yl)-1H- pyrazol-1-yl]azetidin-1- yl}-N- isopropylpyrazine-2- carboxamide | 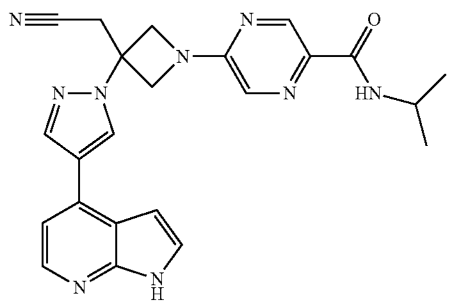 [SMILES: CC(C)NC(=O)c1cnc(N2CC(CC#N)(n3cc(-c4ccnc5[nH]ccc45)cn3)C2)cn1] | + | >10 |
| 18 | US 2013/ 0045963 (Example 45) | {1-(cis-4-{[6-(2- hydroxyethyl)-2- (trifluoromethyl)pyrimi- din-4- yl]oxy}cyclohexyl)-3- [4-(7H-pyrrolo[2,3- d]pyrimidin-4-yl)-1H- pyrazol-1-yl]azetidin-3- yl}acetonitrile | 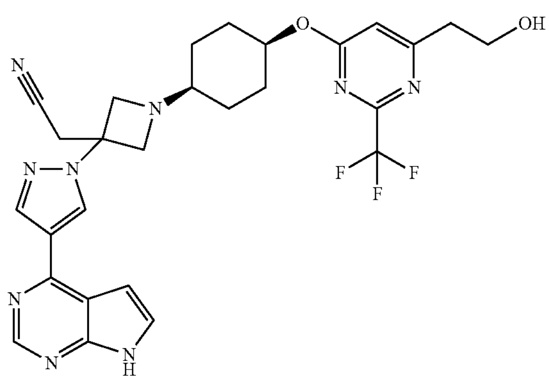 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | US 2013/ 0045963 (Example 65) | {1-(cis-4-{[4- [(ethylamino)methyl]-6- (trifluoromethyl)pyridin- 2-yl]oxy}cyclohexyl)- 3-[4-7H-pyrrolo[2,3- d]pyrimidin-4-yl)-1H- pyrazol-1-yl]azetidin-3- yl}acetonitrile | 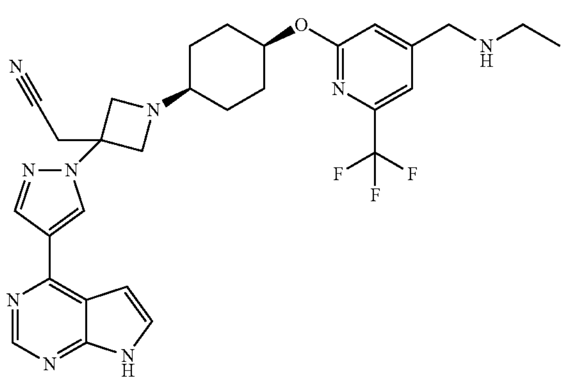 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 20 | US 2013/ 0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 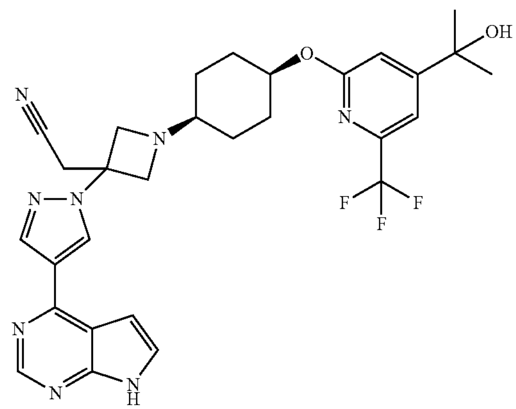 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | US 2013/ 0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 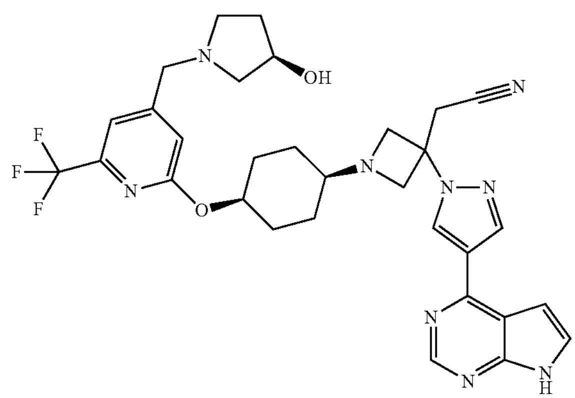 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | US 2013/ 0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 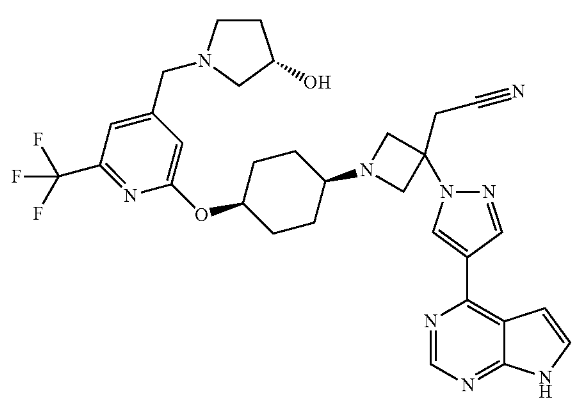 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |

TABLE 1-continued

| Comp. No. | Prep. | Name | Structure | JAK1 IC$_{50}$ (nM) | JAK2/JAK1 |
|---|---|---|---|---|---|
| 23 | US 2014/ 0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 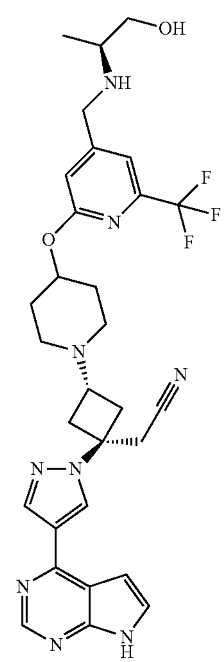 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |
| 24 | US 2014/ 0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 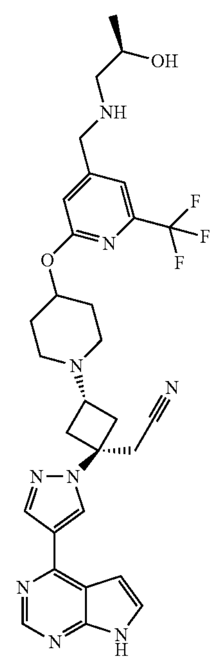 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 25 | US 2014/ 0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 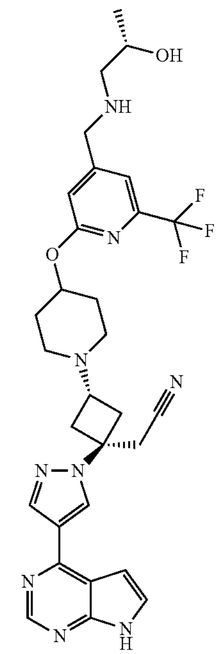 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 26 | US 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 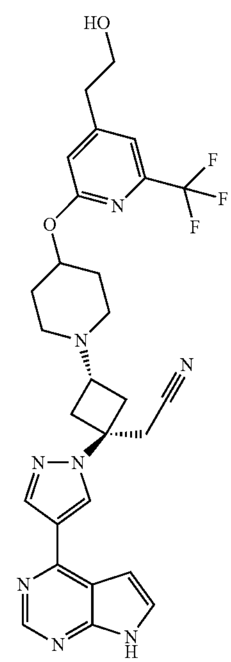 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means < 10 nM (see Example 1 for assay conditions)

++ means ≤ 100 nM (see Example 1 for assay conditions)

+++ means ≤ 300 nM (see Example 1 for assay conditions)

[a] Data for enantiomer 1

[b] Data for enantiomer 2

In some embodiments, the JAK1 inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the JAK1 inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

The synthesis and preparation of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the JAK1 inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK1 inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

In some embodiment, the JAK1 inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrochloric acid salt.

In some embodiment, the JAK1 inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrobromic acid salt.

In some embodiment, the JAK1 inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide sulfuric acid salt.

The synthesis and preparation of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide and the phosphoric acid salt of the same can be found, e.g., in US Patent Publ. No. US 2014/0343030, filed May 16, 2014, which is incorporated herein by reference in its entirety.

In some embodiments, the JAK1 inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile monohydrate.

Synthesis of ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table 1 are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the JAK1 inhibitor is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the JAK1 inhibitor is a compound of Formula I:

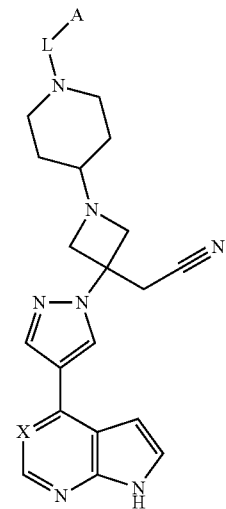

or a pharmaceutically acceptable salt thereof, wherein:
X is N or CH;
L is C(=O) or C(=O)NH;
A is phenyl, pyridinyl, or pyrimidinyl each of which is optionally substituted with 1 or 2 independently selected $R^1$ groups; and
each $R^1$ is, independently, fluoro, or trifluoromethyl.

In some embodiments, the compound of Formula I is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the compound of Formula I is 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide, or a pharmaceutically acceptable salt thereof.

In some embodiments, the compound of Formula I is [3-[4-(7H-pyrrolo[2,3-d]pyrimidin-4-yl)-1H-pyrazol-1-yl]-1-(1-{[2-(trifluoromethyl)pyrimidin-4-yl]

carbonyl}piperidin-4-yl)azetidin-3-yl]acetonitrile, or a pharmaceutically acceptable salt thereof.

In some embodiments, the JAK1 inhibitor is a compound of Formula II:

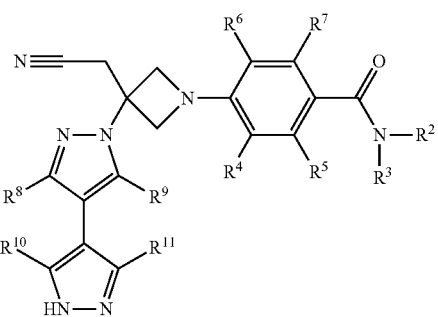

or a pharmaceutically acceptable salt thereof, wherein:
$R^2$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;
$R^3$ is H or methyl;
$R^4$ is H, F, or Cl;
$R^5$ is H or F;
$R^6$ is H or F;
$R^7$ is H or F;
$R^8$ is H or methyl;
$R^9$ is H or methyl;
$R^{10}$ is H or methyl; and
$R^{11}$ is H or methyl.

In some embodiments, the compound of Formula II is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK1 inhibitor is a compound of Formula III:

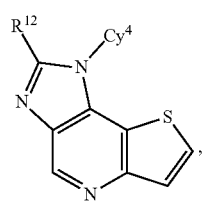

or a pharmaceutically acceptable salt thereof, wherein:
$Cy^4$ is a tetrahydro-2H-pyran ring, which is optionally substituted with 1 or 2 groups independently selected from CN, OH, F, Cl, $C_{1-3}$ alkyl, $C_{1-3}$ haloalkyl, CN—$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl; and
$R^{12}$ is —$CH_2$—OH, —$CH(CH_3)$—OH, or —$CH_2$—$NHSO_2CH_3$.

In some embodiments, the compound of Formula III is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In another embodiment, the present application provides a method of treating cutaneous lupus erythematosus (CLE) in a patient in need thereof, comprising topically administering to the skin of the patient a topical formulation comprising 0.5% (w/w) to 1.5% (w/w) on a free base basis of ruxolitinib, or a pharmaceutically acceptable salt thereof. In another embodiment, the present application provides a method of treating cutaneous lichen planus (LP) in a patient in need thereof, comprising topically administering to the skin of the patient a topical formulation comprising 0.5% (w/w) to 1.5% (w/w) on a free base basis of ruxolitinib, or a pharmaceutically acceptable salt thereof. In some embodiments, the ruxolitinib, or the pharmaceutically acceptable salt thereof, is ruxolitinib phosphate. In some embodiments, the topical formulation is a cream formulation. In some embodiments, 0.75% (w/w) on a free base basis of the ruxolitinib, or the pharmaceutically acceptable salt thereof, is present. In some embodiments, 1.5% (w/w) on a free base basis of the ruxolitinib, or the pharmaceutically acceptable salt thereof, is present. In some embodiments, the administering is twice per day (BID).

One or more constituent atoms of the compounds described herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

Accordingly, in some embodiments, the JAK1 inhibitor (e.g., the JAK1 selective inhibitor) is a compound, wherein one or more hydrogen atoms in the compound are replaced by deuterium atoms, or a pharmaceutically acceptable salt thereof.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like.

As used herein, the term "alkylene", employed alone or in combination with other terms, refers to a divalent alkyl linking group, which can be branched or straight-chain, where the two substituents may be attached any position of the alkylene linking group. Examples of alkylene groups include, but are not limited to, ethan-1,2-diyl, propan-1,3-diyl, propan-1,2-diyl, and the like.

As used herein, the term "HO—$C_{1-3}$-alkyl" refers to a group of formula -alkylene-OH, wherein said alkylene group has 1 to 3 carbon atoms.

As used herein, the term "CN—$C_{1-3}$ alkyl" refers to a $C_{1-3}$ alkyl substituted by a cyano group.

As used herein, the term "amino" refers to a group of formula —$NH_2$.

As used herein, the term "di($C_{1-3}$-alkyl)amino" refers to a group of formula —$N(alkyl)_2$, wherein the two alkyl groups each has, independently, 1 to 3 carbon atoms.

As used herein, the term "$C_{1-3}$ alkylamino" refers to a group of formula —NH(alkyl), wherein the alkyl group has 1 to 3 carbon atoms.

As used herein, the term "di($C_{1-3}$ alkyl)aminosulfonyl" refers to a group of formula —$S(O)_2N(alkyl)_2$, wherein each alkyl group independently has 1 to 3 carbon atoms.

As used herein, the term "$C_{1-3}$ alkylsulfonyl" refers to a group of formula —$S(O)_2$-alkyl, wherein the alkyl group has 1 to 3 carbon atoms.

As used herein, "halo" or "halogen", employed alone or in combination with other terms, includes fluoro, chloro, bromo, and iodo. In some embodiments, the halo group is fluoro or chloro.

As used herein, the term "$C_{n-m}$ haloalkyl", employed alone or in combination with other terms, refers to a $C_{n-m}$ alkyl group having up to {2(n to m)+1} halogen atoms which may either be the same or different. In some embodiments, the halogen atoms are fluoro atoms. In some embodiments, the alkyl group has 1-6 or 1-3 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

As used herein, the term "$C_{1-3}$ fluoroalkyl" refers to a $C_{1-3}$ alkyl group that may be partially or completely substituted by fluoro atoms.

As used herein, the term "$C_{3-6}$ cycloalkyl", employed alone or in combination with other terms, refers to a non-aromatic monocyclic hydrocarbon moiety, having 3-6 carbon atoms, which may optionally contain one or more alkenylene groups as part of the ring structure. One or more ring-forming carbon atoms of a cycloalkyl group can be oxidized to form carbonyl linkages. Exemplary $C_{3-6}$ cycloalkyl groups include cyclopropyl, cyclobutyl, cyclopentyl, cyclohexyl, cyclopentenyl, cyclohexenyl, cyclohexadienyl, and the like. In some embodiments, the cycloalkyl group is cyclopropyl, cyclobutyl, cyclopentyl, or cyclohexyl.

As used herein, the term "$C_{3-6}$ cycloalkyl-$C_{1-3}$ alkyl" refers to a group of formula —$C_{1-3}$ alkylene-$C_{3-6}$ cycloalkyl.

The compounds described herein can be asymmetric (e.g., having one or more stereocenters). All stereoisomers, such as enantiomers and diastereomers, are intended unless otherwise indicated. Compounds that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present application. Cis and trans geometric isomers of the compounds of the present application are described and may be isolated as a mixture of isomers or as separated isomeric forms. In some embodiments, the compound has the (R)-configuration. In some embodiments, the compound has the (S)-configuration.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution. For example, it will be recognized that the following pyrazole ring may form two tautomers:

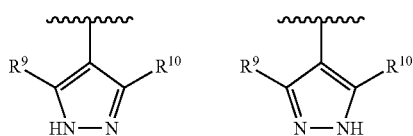

It is intended that the claims cover both tautomers.

All compounds, and pharmaceutically acceptable salts thereof, can be found together with other substances such as water and solvents (e.g. hydrates and solvates) or can be isolated.

In some embodiments, the compounds described herein, or salts thereof, are substantially isolated. By "substantially isolated" is meant that the compound is at least partially or substantially separated from the environment in which it was formed or detected. Partial separation can include, for example, a composition enriched in the compounds described herein. Substantial separation can include compositions containing at least about 50%, at least about 60%, at least about 70%, at least about 80%, at least about 90%, at least about 95%, at least about 97%, or at least about 99% by weight of the compounds described herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

As used herein, the term "contacting" refers to the bringing together of indicated moieties in an in vitro system or an in vivo system. For example, "contacting" a JAK with a compound of the invention includes the administration of a compound of the present application to an individual or patient, such as a human, having a JAK, as well as, for example, introducing a compound of the invention into a sample containing a cellular or purified preparation containing the JAK.

As used herein, the term "subject", "individual" or "patient," used interchangeably, refers to any animal, including mammals, preferably mice, rats, other rodents, rabbits, dogs, cats, swine, cattle, sheep, horses, or primates, and most preferably humans. In some embodiments, the "subject," "individual," or "patient" is in need of said treatment.

In some embodiments, the inhibitors are administered in a therapeutically effective amount. As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease; or (3) preventing the disease, condition or disorder in an individual who may be predisposed to the disease, condition or disorder but does not yet experience or display the pathology or symptomatology of the disease. In some embodiments, treating refers to inhibiting or ameliorating the disease. In some embodiments, treating is preventing the disease.

Combination Therapies

The methods described herein can further comprise administering one or more additional therapeutic agents. The one or more additional therapeutic agents can be administered to a patient simultaneously or sequentially.

In some embodiments, the additional therapeutic agent is an antibiotic. In some embodiments, the antibiotic is clindamycin, doxycycline, minocycline, trimethoprim-sulfamethoxazole, erythromycin, metronidazole, rifampin, moxifloxacin, dapsone, or a combination thereof. In some embodiments, the antibiotic is clindamycin, doxycycline, minocycline, trimethoprim-sulfamethoxazole, or erythromycin in combination with metronidazole. In some embodiments, the antibiotic is a combination of rifampin, moxifloxacin, and metronidazole. In some embodiments, the antibiotic is a combination of moxifloxacin and rifampin.

In some embodiments, the additional therapeutic agent is a retinoid. In some embodiments, the retinoid is etretinate, acitretin, or isotretinoin.

In some embodiments, the additional therapeutic agent is a steroid. In some embodiments, the additional therapeutic agent is a corticosteroid. In some embodiments, the steroid is such as triamcinolone, dexamethasone, fluocinolone, cortisone, prednisone, prednisolone, or flumetholone.

In some embodiments, the additional therapeutic agent is an anti-TNF-alpha agent. In some embodiments, the anti-TNF-alpha agent is an anti-TNF-alpha antibody. In some embodiments, the anti-TNF-alpha agent is infliximab or etanercept, or adalimumab.

In some embodiments, the additional therapeutic agent is an immunosuppressant. In some embodiments, the immunosuppressant is methotrexate or cyclosporin A. In some embodiments, the immunosuppressant is mycophenolate mofetil or mycophenolate sodium.

In some embodiments, the additional therapeutic agent is finasteride, metformin, adapalene or azelaic acid.

In some embodiments, the method further comprises administering an additional therapeutic agent selected from IMiDs, an anti-IL-6 agent, a hypomethylating agent, and a biologic response modifier (BRM).

Generally, a BRM is a substances made from living organisms to treat disease, which may occur naturally in the body or may be made in the laboratory. Examples of BRMs include IL-2, interferon, various types of colony-stimulating factors (CSF, GM-CSF, G-CSF), monoclonal antibodies such as abciximab, etanercept, infliximab, rituximab, trasturzumab, and high dose ascorbate.

In some embodiments, the hypomethylating agent is a DNA methyltransferase inhibitor. In some embodiments, the DNA methyltransferase inhibitor is selected from 5 azacytidine and decitabine.

Generally, IMiDs are as immunomodulatory agents. In some embodiments, the IMiD is selected from thalidomide, lenalidomide, pomalidomide, CC-11006, and CC-10015.

In some embodiments, the method further comprises administering an additional therapeutic agent selected from anti-thymocyte globulin, recombinant human granulocyte colony-stimulating factor (G CSF), granulocyte-monocyte CSF (GM-CSF), an erythropoiesis-stimulating agent (ESA), and cyclosporine.

In some embodiments, the method further comprises administering an additional JAK inhibitor to the patient. In some embodiments, the additional JAK inhibitor is selected from a JAK2 inhibitor (e.g., a selective JAK2 inhibitor), a JAK/JAK2 inhibitor, a JAK3 inhibitor (e.g., a selective JAK3 inhibitor), and a JAK1/JAK3 inhibitor, or a pharmaceutically acceptable salt of any of the aforementioned.

In some embodiments, the additional JAK inhibitor is a JAK1/JAK2 inhibitor. In some embodiments, the JAK1/JAK2 inhibitor is selective for JAK1 and JAK2 over JAK3 and TYK2. In some embodiments, the JAK/JAK2 inhibitor is 3-cyclopentyl-3-[4-(7H-pyrrolo[2,3-d]pyrimidin-4-yl)-1H-pyrazol-1-yl]propanenitrile, or a pharmaceutically acceptable salt thereof. In some embodiments, the JAK1/JAK2 inhibitor is (3R)-3-cyclopentyl-3-[4-(7H-pyrrolo[2,3-d]pyrimidin-4-yl)-1H-pyrazol-1-yl]propanenitrile (ruxolitinib), or a pharmaceutically acceptable salt thereof. Ruxolitinib has an IC$_{50}$ of less than 10 nM at 1 mM ATP at JAK1 and JAK2. 3-Cyclopentyl-3-[4-(7H-pyrrolo[2,3-d]pyrimidin-4-yl)-1H-pyrazol-1-yl]propanenitrile and ruxolitinib can be made by the procedure described in U.S. Pat. No. 7,598,257 (Example 67), filed Dec. 12, 2006, which is incorporated herein by reference in its entirety. In some embodiments, the JAK/JAK2 inhibitor is (3R)-3-cyclopentyl-3-[4-(7H-pyrrolo[2,3-d]pyrimidin-4-yl)-1H-pyrazol-1-yl]propanenitrile phosphoric acid salt. The phosphoric acid salt can be made as described in U.S. Pat. No. 8,722,693, which is incorporated herein by reference in its entirety. In some embodiments, the JAK1/JAK2 inhibitor is barcitinib, or a pharmaceutically acceptable salt thereof. In some embodiments, the JAK1/JAK2 inhibitor is barcitinib.

In some embodiments, the additional JAK1 inhibitor is a JAK1/JAK3 inhibitor. In some embodiments, the JAK1/JAK3 inhibitor is tofacitinib, or a pharmaceutically acceptable salt thereof. In some embodiments, the JAK1/JAK3 inhibitor is tofacitinib.

In some embodiments, the JAK1/JAK2 inhibitor can be an isotopically-labeled compound, or a pharmaceutically acceptable salt thereof. An "isotopically" or "radio-labeled" compound is a compound wherein one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms, such as —CD$_3$ being substituted for —CH$_3$).

Accordingly, in some embodiments, the JAK1/JAK2 inhibitor is a compound, wherein one or more hydrogen atoms in the compound are replaced by deuterium atoms, or a pharmaceutically acceptable salt thereof.

In some embodiments, the JAK1/JAK2 inhibitor is ruxolitinib, wherein one or more hydrogen atoms are replaced by deuterium atoms, or a pharmaceutically acceptable salt thereof. In some embodiments, the JAK1/JAK2 inhibitor is any of the compounds in U.S. Pat. No. 9,249,149, which is incorporated herein by reference in its entirety, or a pharmaceutically acceptable salt thereof. In some embodiments, the inhibitor of JAK1/JAK2 is CTP-543, or a pharmaceutically acceptable salt thereof.

In some embodiments, the JAK1/JAK2 inhibitor is a compound of Formula IV:

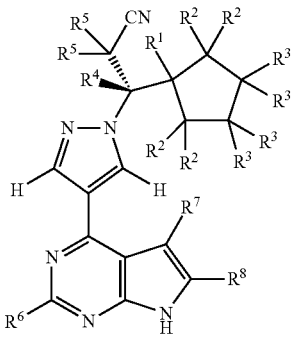

IV or a pharmaceutically acceptable salt thereof, wherein:
R$^1$ is selected from H and D;
each R$^2$ is independently selected from H and D, provided that each R attached to a common carbon is the same;
each R$^3$ is independently selected from H and D, provided that each R$^3$ attached to a common carbon is the same;
R$^4$ is selected from and D;
each R$^5$ is the same and is selected from H and D; and
R$^6$, R$^7$, and R$^8$ are each independently selected from H and D; provided that when R$^1$ is H, each R$^2$ and each R$^3$ are H, R$^4$ is H, and each of R$^6$, R$^7$, and R$^8$ is H, then each R$^5$ is D.

In some embodiments, the JAK1/JAK2 inhibitor is a compound of Formula IV selected from the following compounds 100-130 in the table below (wherein R$^6$, R$^7$, and R$^8$ are each H), or a pharmaceutically acceptable salt thereof. In some embodiments, the JAK1/JAK2 inhibitor is a compound of Formula IV selected from the following compounds 200-231 in the table below (wherein R$^6$, R$^7$, and R$^8$ are each D), or a pharmaceutically acceptable salt thereof.

| Compound | R$^1$ | Each R$^2$ | Each R$^3$ | R$^4$ | Each R$^5$ |
|---|---|---|---|---|---|
| 100 | H | H | H | D | H |
| 101 | H | H | H | H | D |
| 102 | H | H | H | D | D |
| 103 | H | H | D | H | H |
| 104 | H | H | D | D | H |
| 105 | H | H | D | H | D |
| 106 | H | H | D | D | D |
| 107 | H | D | H | H | H |
| 108 | H | D | H | D | H |
| 109 | H | D | H | H | D |
| 110 | H | D | H | D | D |
| 111 | H | D | D | H | H |
| 112 | H | D | D | D | H |

-continued

| Compound | R$^1$ | Each R$^2$ | Each R$^3$ | R$^4$ | Each R$^5$ |
|---|---|---|---|---|---|
| 113 | H | D | D | H | D |
| 114 | H | D | D | D | D |
| 115 | D | H | H | H | H |
| 116 | D | H | H | H | D |
| 117 | D | H | H | H | D |
| 118 | D | H | H | D | D |
| 119 | D | H | D | H | H |
| 120 | D | H | D | H | H |
| 121 | D | H | D | H | D |
| 122 | D | H | D | D | D |
| 123 | D | D | H | H | H |
| 124 | D | D | H | H | H |
| 125 | D | D | H | H | D |
| 126 | D | D | H | D | D |
| 127 | D | D | D | H | H |
| 128 | D | D | D | D | H |
| 129 | D | D | D | H | D |
| 130 | D | D | D | D | D |
| 200 | H | H | H | D | D |
| 201 | H | H | H | D | D |
| 202 | H | H | D | H | D |
| 203 | H | H | D | H | H |
| 204 | H | H | D | H | H |
| 205 | H | H | D | H | D |
| 206 | H | H | D | H | D |
| 207 | H | D | H | H | H |
| 208 | H | D | H | D | H |
| 209 | H | D | H | D | D |
| 210 | H | D | H | D | D |
| 211 | H | D | D | H | H |
| 212 | H | D | D | D | H |
| 213 | H | D | D | H | D |
| 214 | H | D | D | D | D |
| 215 | D | H | H | H | H |
| 216 | D | H | H | D | H |
| 217 | D | H | H | H | D |
| 218 | D | H | H | D | D |
| 219 | D | H | H | H | H |
| 220 | D | H | D | D | H |
| 221 | D | H | D | H | D |
| 222 | D | H | D | D | D |
| 223 | D | D | H | H | H |
| 224 | D | D | H | D | H |
| 225 | D | D | H | H | D |
| 226 | D | D | H | D | D |
| 227 | D | D | D | H | H |
| 228 | D | D | D | D | H |
| 229 | D | D | D | H | D |
| 230 | D | D | D | D | D |
| 231 | H | H | H | H | H |

In some embodiments, the JAK1/JAK2 inhibitor is baricitinib, wherein one or more hydrogen atoms are replaced by deuterium atoms, or a pharmaceutically acceptable salt thereof. In some embodiments, the JAK1/JAK2 inhibitor is any of the compounds in U.S. Pat. No. 9,540,367 (which is incorporated herein by reference in its entirety), or a pharmaceutically acceptable salt thereof.

In some embodiments, the additional JAK inhibitor is selected from baricitinib, tofacitinib, oclacitinib, filgotinib, gandotinib, lestaurtinib, momelotinib, bacritinib, PF-04965842, upadacitinib, peficitinib, fedratinib, cucurbitacin I, ATI-501 (Aclaris), ATI-502 (Aclaris), JTE-052 (i.e., delgocitinib; Leo Pharma and Japan Tobacco), and CHZ868.

Additional agents including, but not limited to, anti-inflammatory agents, immunosuppressants, PI3Kδ inhibitors, mTor inhibitors, Bcr-Abl inhibitors, Flt-3 inhibitors, RAF inhibitors, and FAK kinase inhibitors (e.g., those described in WO 2006/056399, which is incorporated herein by reference in its entirety), or other agents can be used in combination with the JAK1 inhibitors described herein for treatment of cutaneous lupus erythematosus (CLE). The one or more additional agents can be administered to a patient simultaneously or sequentially.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, one or more of the JAK1 inhibitors described herein can be used in combination with one or more other kinase inhibitors including imatinib, particularly for treating patients resistant to imatinib or other kinase inhibitors.

In some embodiments, the additional therapeutic agent is fluocinolone acetonide (Retisert®) or rimexolone (AL-2178, Vexol, Alcon).

In some embodiments, the additional therapeutic agent is cyclosporine (Restasis®).

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodo-phenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), actemra, gemcitabine, oxaliplatin, L-asparaginase, or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, or an mTOR inhibitor. In some embodiments, the additional therapeutic agent is a tetracycline derivative (e.g., minocycline or doxycycline). In some embodiments, the additional therapeutic agent binds to FKBP12.

In some embodiments, the additional therapeutic agent is an alkylating agent or DNA cross-linking agent; an antimetabolite/demethylating agent (e.g., 5-flurouracil, capecitabine or azacitidine); an anti-hormone therapy (e.g., hormone receptor antagonists, SERMs, or aromotase inhibitor); a mitotic inhibitor (e.g. vincristine or paclitaxel); an topoisomerase (I or II) inhibitor (e.g. mitoxantrone and irinotecan); an apoptotic inducers (e.g. ABT-737); a nucleic acid therapy (e.g. antisense or RNAi); nuclear receptor ligands (e.g., agonists and/or antagonists: all-trans retinoic acid or bexarotene); epigenetic targeting agents such as histone deacetylase inhibitors (e.g. vorinostat), hypomethylating agents (e.g. decitabine); regulators of protein stability such as Hsp90 inhibitors, ubiquitin and/or ubiquitin like conjugating or deconjugating molecules; or an EGFR inhibitor (erlotinib).

In some embodiments, the additional therapeutic agent is selected from an antibiotic, an antiviral, an antifungal, an anesthetic, an anti-inflammatory agent (e.g., steroidal and non-steroidal anti-inflammatory agents), and an anti-allergic agent. Examples of suitable agents include, but are not limited to, aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Pharmaceutical Formulations and Dosage Forms

When employed as pharmaceuticals, the JAK1 inhibitors provided herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including intradermal, transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, dermal patches, solutions, suspensions, foams, ointments, lotions, creams, gels, drops, suppositories, sprays, liquids, and powders. Conventional pharmaceutical carriers, aqueous, powder or oily bases, thickeners and the like may be necessary or desirable. In some embodiments, the composition is formulated for topical administration by transdermal patch, dermal patch, solution, suspension, gel, cream, ointment, lotion, spray, foam, liquid, drops, suppository, and powder. In some embodiments, the composition is formulated for topical administration by transdermal patch. In some embodiments, the composition is formulated for topical administration by dermal patch. In some embodiments, the composition is formulated as a foam (e.g., for topical administration).

For the treatment of skin disorders such as cutaneous lupus erythematosus (CLE), topical drugs which are able to penetrate the skin barrier and provide limited systemic effects are of particular importance.

Topical (dermal/intradermal) formulations are typically solutions, suspensions, gels, creams, ointments, lotions, sprays and foams. Preferred topical formulations should be physically and chemically stable, not cause skin irritation, and deliver the active agent (e.g., a selective JAK1 inhibitor, or a pharmaceutically acceptable salt thereof, as described herein) at the appropriate layer of the skin in concentrations that would result in therapeutic response, with limited systemic exposure.

In some embodiments, the administration is topical and comprised of formulations with one or more pharmaceutically (e.g., dermatologically) acceptable excipients. Examples of dermatologically acceptable excipients include, but are not limited to, a pH adjusting agents, chelating agents, preservatives, co-solvents, penetration enhancers, humectants, thickening, gelling, viscosity building agents, surfactants, propellants, fragrance, colorants, or any combination or mixture thereof. In some embodiments, the topical formulation is administered locally to the patient (e.g., administered at the site of a lesion).

In some embodiments, the pH-adjusting agent is selected from an acid, an acid salt, a base, a base salt, and a buffer, or any mixture thereof. Exemplary acids include, but are not limited to, lactic acid, acetic acid, citric acid, and benzoic acid, and salts thereof. Exemplary bases include, but are not limited to, trolamine, tromethamine, and salts thereof. Exemplary buffers include, but are not limited to, citrate/citric acid, acetate/acetic acid, edetate/edetic acid, lactate/lactic acid, and the like.

In some embodiments, the chelating agent is a single excipient. In some embodiments, the chelating agent is a mixture of two or more chelating agents. Exemplary chelating agents include, but are not limited to, ethylenediaminetetraacetic acid (EDTA), or a salt thereof. In some embodiments, the chelating agent comprises a mixture of a chelating agent and an antioxidant, wherein the chelating agent and antioxidant prevent, minimize, or reduce oxidative degradation reactions in the composition. Exemplary antioxidants include, but are not limited to, butylated hydroxytoluene (BHT), butylated hydroxyanisole (BHA), tocopherol, and propyl gallate.

In some embodiments, the composition comprises one or more preservatives. In some embodiments, the composition comprises a mixture of two or more preservatives. In some embodiments, the composition comprises one to five preservatives. Exemplary preservatives include, but are not limited to, benzyl alcohol, phenonyexthanol, methyl paraben, ethyl paraben, propyl paraben, butyl paraben, and imidazolidinyl urea.

In some embodiments, the composition comprises one or more co-solvents. In some embodiments, the composition comprises a mixture of two or more co-solvents. In some embodiments, the composition comprises one to five co-solvents. Exemplary solvents include, but are not limited to, water, propylene glycol, diethylene glycol monoethyl ether, dimethyl isosorbide, ethyl alcohol, isopropyl alcohol, benzyl alcohol, propanediol, propylene glycol, polyethylene glycols (e.g., polyethylene glycol 200, polyethylene glycol 300, polyethylene glycol 400, and the like). In some embodiments, the solvent is a non-water soluble agent. Exemplary non-water soluble agents include, but are not limited to, diethyl sebacate, diisopropyl adipate, isopropyl myristate, isopropyl palmitate, and medium chain triglycerides.

In some embodiments, the composition comprises one or more penetration enhancers. In some embodiments, the composition comprises a mixture of two or more penetration enhancers. In some embodiments, the composition comprises one to five penetration enhancers. The penetration enhancers can act as both a solvent and a penetration enhancer. Exemplary penetration enhancers include, but are not limited to, fatty acids, fatty acid esters, fatty alcohols, pyrrolidones, sulfoxides, alcohols, diols and polyols, or any mixture thereof. In some embodiments, a co-solvent provided herein is a penetration enhancer.

In some embodiments, the composition comprises one or more thickening, gelling, or viscosity building agents. In some embodiments, the composition comprises a mixture of two or more thickening, gelling, or viscosity building agents. In some embodiments, the composition comprises one to five thickening, gelling, or viscosity building agents. Exemplary thickening, gelling, or viscosity building agents include, but are not limited to, cellulosic derivatives (e.g., hydroxyethylcellulose (HEC), carboxymethylcellulose, hydroxypropylcellulose (HPC), and hydroxypropyl methylcellulose (HPMC), and polyvinylpyrrolidone (PVP).

The surfactant is a compound that lowers the surface tension between two liquids or between a liquid and a solid. Surfactant may be a mixture of two or more surfactants. Exemplary surfactants include, but are not limited to, ethoxylated fatty alcohol ether (e.g., steareth-2, steareth-10, steareth-20, ceteareth-2, ceteareth-10, and the like), PEG esters (e.g., PEG-4 dilaurate, PEG-20 stearate, and the like), Glyceryl esters or derivatives thereof (e.g., glyceryl dioleate, glyceryl stearate, and the like), polymeric ethers (e.g., poloxamer 124, poloxamer 181, poloxamer 182, and the like), sorbitan derivatives (e.g., polysorbate 80, sorbitan monostearate, and the like), fatty alcohols (e.g., cetyl alcohol, stearyl alcohol, cetearyl alcohol, and the like), and emulsifying wax (e.g., emulsifying wax NF, mixtures of mixture of cetearyl alcohol and polysorbate 60, and the like).

In some embodiments, the administration is topical administration to the skin.

In some embodiments, the administration is oral.

In some embodiments, administration of a topical composition comprising a selective JAK1 inhibitor provided herein to a patient provides a systemic exposure ($C_{max}$) at steady state of about 5% or less of the applied dose, e.g., about 4% or less, about 3% or less, about 2% or less, about 1% or less, and the like. In some embodiments, administration of a topical composition comprising a selective JAK1 inhibitor provided herein to a patient provides a systemic exposure ($C_{max}$) at steady state of about 1% or less of the applied dose, This invention also includes pharmaceutical compositions which contain, as the active ingredient, a JAK1 inhibitors provided herein, or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The JAK1 inhibitors provided herein may be milled using known milling procedures such as wet milling to obtain a particle size appropriate for tablet formation and for other formulation types. Finely divided (nanoparticulate) preparations of the JAK1 inhibitors can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose, and polyethylene oxide. In some embodiments, the composition comprises at least one compound described herein, or a pharmaceutically acceptable salt thereof, and microcrystalline cellulose, lactose monohydrate, and hydroxypropyl methylcellulose. In some embodiments, the composition comprises at least one compound described herein, or a pharmaceutically acceptable salt thereof, and microcrystalline cellulose, lactose monohydrate, and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 1 to about 1,000 mg, from about 1 mg to about 100 mg, from 1 mg to about 50 mg, and from about 1 mg to 10 mg of active ingredient. Preferably, the dosage is from about 1 mg to about 50 mg or about 1 mg to about 10 mg of active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions comprise from about 1 to about 1,000 mg, from about 1 mg to about 100 mg, from 1 mg to about 50 mg, and from about 1 mg to 10 mg of active ingredient. Preferably, the compositions comprise from about 1 mg to about 50 mg or about 1 mg to about 10 mg of active ingredient. One having ordinary skill in the art will appreciate that this embodies compounds or compositions containing about 1 mg to about 10 mg, about 1 mg to about 20 mg, about 1 mg to about 25 mg, about 1 mg to about 50 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present application. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present application (e.g. a JAK1 inhibitor provided herein).

The tablets or pills of the present application can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical (e.g., intradermal) administration provides the advantage of treating the skin disorder locally, minimizing potential adverse events associated with systemic exposure, and allowing an easier discontinuation of the therapy, if necessary. Additionally, some topical dosage forms such as creams, ointments, and gels have the benefit of excipients that may act as emollients or occlusive agents, which can increase patient well-being and compliance during the treatment period. Other dosage routes such as oral, parenteral, and inhalation may lead to supratherapeutic systemic drug levels, increased likelihood of adverse events, drug-drug interactions, and generation of active/toxic metabolites, which may result in treatment discontinuation and inadequate patient compliance.

Topical formulations intended for dermal delivery are typically solutions, suspensions, gels, creams, ointments, lotions, sprays, and foams and can contain one or more conventional carriers as described herein. The formulation composition should be prepared with the goal of delivering the active ingredient to the appropriate layer(s) of the skin, minimizing systemic exposure, and preventing skin irritation. Additionally the pharmaceutical composition should be physically and chemically stable. Depending on the selected dosage form, one or more additional excipients as described herein may be necessary, e.g., pH adjusting agents, chelating agents, preservatives, co-solvents, penetration enhancers, humectants, thickening, gelling, viscosity building agents, surfactants, propellants, fragrances, colorants, or any combination or mixture thereof.

In some embodiments, topical formulations can contain one or more conventional carriers as described herein. In some embodiments, ointments can contain water and one or more hydrophobic carriers selected from, for example, liquid paraffin, polyoxyethylene alkyl ether, propylene glycol, white petrolatum, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g, which are optionally associated with instructions for the treatment of cutaneous lupus erythematosus (CLE).

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from cutaneous lupus erythematosus (CLE) in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present application can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents, examples of which are listed hereinabove.

Kits

The present application also includes pharmaceutical kits useful, for example, in the treatment and/or prevention of cutaneous lupus erythematosus (CLE), which include one or more containers containing a pharmaceutical composition comprising a therapeutically effective amount of a JAK1 inhibitor described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

All statistical analysis of in vitro experiments were performed with GraphPad prism software (version 7) using Kruskal-Wallis-Test and Mann-Whitney U test. Gene expression was analyzed with Partek Flow genomic analysis software and Subio Platform software v1.22.5266 using Welch's t-test. Confidence intervals were determined at 95%. P<0.05 was considered to be "significant" (*), p<0.01 to be "highly significant" (**). KEGG pathways were mapped to differentially expressed genes using DAVID v6.8 (Database for Annotation, Visualization and Integrated Discovery).

Example 1. In Vitro JAK Kinase Assay

JAK1 inhibitors that can be used for the treatment of cytokine-related diseases or disorders are tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag are expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$ s of compounds are measured for each kinase in the 40 µL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions is 1 mM. Reactions are carried out at room temperature for 1 hour and then stopped with 20 µL 45 mM EDTA, 300 nM SA-APC, 6 nM Eu-Py20 in assay buffer (Perkin Elmer, Boston, MA). Binding to the Europium labeled antibody takes place for 40 minutes and HTRF signal was measured on a Fusion plate reader (Perkin Elmer, Boston, MA). The compounds in Table 1 were tested in this assay and shown to have the $IC_{50}$ values in Table 1.

Example 2. Activated JAK1 is Strongly Expressed in Human CLE Skin Lesions

To investigate the specific role of JAK1-mediated signaling in CLE, phosphorylated JAK1 (pJAK1) expression in lesional skin (SCLE and CDLE subsets) was compared to Lichen planus (LP) as well as healthy controls. All punch biopsies of the different inflammatory skin disorders (N=34) were taken for diagnostic purposes from active skin lesions. Healthy controls (N=9) were taken from unaffected skin taken from plastical surgery. Skin samples were fixed with 4% formalin overnight or fixed in frozen nitrogen and proceeded for immunohistochemistry or RNA isolation. RNA was processed by the Next Generation Sequencing (NGS) Core Facility of the Medical Faculty of the University of Bonn using the QuantSeq 3'-mRNA Library Prep Kit by Lexogen. Illumina HiSeq 2500 was used for RNA sequencing (Standard 3'RNA seq with 50 cycles)

In CLE skin lesions, the expression of pJAK1 was significantly increased in keratinocytes from stratum basale to stratum granulosum and in dermal infiltrating immune cells. It was also observed that pJAK1 was significantly enhanced in Lichen planus, an autoimmune disease sharing common histological features with CLE.

Example 2. JAK/STAT-Associated Innate Inflammatory Pathways are Significantly Activated in Human CLE Skin Samples of lesional skin from CLE patients were H&E stained to confirm the clinical diagnosis in each case by an experienced dermatopathologist. Immunohistochemistry was performed using the REAL™ Detection Systems with Fast Red as chromogen (Agilent, Santa Clara, USA) with specific antibodies for pJAK (ABIN196869, antibodies-online), CXCL10 (ab9807, Cambridge, UK), MxA (M143, Haller, Freiburg, Germany) and CD45 (550539, BD, New Jersey). The expression was scored semiquantitatively from 0≙ weak to 3≙ strong (Wenzel et al. *J. Pathol.* 2005, 205:435-442). Immunofluorescence analyses of JAK1-phosphorylation detected by anti-rabbit Rhodamine Red-X (711-295-152; Jackson ImmunoResearch, Baltimore, MD, USA) and DAPI (D9542, Sigma-Aldrich) were performed using a high-resolution microscope (Axio Observer Z1, Zeiss, Germany).

Within CLE lesional skin expression analysis revealed a significant activation of genes associated with both innate and adaptive immune pathways compared to healthy controls. In particular, genes of LE-associated proinflammatory chemokines (CXCL10,9,11) and other IFN-regulated proteins (OASL, OAS2, Mx1) as well as key drivers in cell death and B-cell activation (CXCR3, CASP10, AIM2, TRAIL, BLyS) were highly expressed. JAK/STAT signaling is a critical regulator of inflammatory gene transcription, therefore gene expression of STAT1 in LE lesions was also significantly increased, as shown in FIG. 1C. Corresponding to individual genes upregulated innate immune pathways included JAK/STAT pathway and associated cytokine-/chemokine signaling as well as upstream TLR-dependent and -independent DAMP-recognition pathways, as shown in FIG. 1D.

Example 3. INCB039110 Significantly Inhibits JAK1-Phosphorylation in Cultured Immortalized Human Keratinocytes To analyze the functional principle and effect of JAK inhibition, the following established in vitro models of CLE were used. Immortalized keratinocytes (HaCaT), were acquired from CLS Cell Lines Service GmbH, Eppelheim, Germany), normal human epidermal keratinocytes (NHEKs, FC-0025) and Human epidermis equivalents (epiCS, CS-1001) from CellSystems, Troisdorf, Germany. These cell lines were cultured according the manufactures protocols. Cultured keratinocytes were stimulated with endogenous nucleic acids (eNA, 1.25 µg/mL) isolated from unstimulated keratinocytes using the "Genomic DNA from tissue" kit (Machery-Nagel, Dueren, Germany). Lipofectamine 2000 (Invitrogen, Carlsbad, USA) functioned as a transfection reagent (2.5 µL/mL). INCB039110, as well as ruxolitinib (Selleckchem, Eching, Germany) were added at a final concentration of 1 µM; JAK3 selective FM-381 was used as recommended (100 nm) (see e.g., Forster et al, *Cell Chem. Biol.* 2016, 23:1335-1340). All experiments were implemented in biological triplicates. Enzyme-linked immunosorbent assays for human CXCL10 (DY266-05 R&D systems) were performed using DuoSet Ancillary Reagent Kit 2 (DY008 R&D systems) according to the supplied protocol, measured by Synergy HT Multi-Detection Multiplate Reader (BioTek, Winooski, VT, USA) and read out with Gen5 software (version 1.11.5).

Figure 2B:
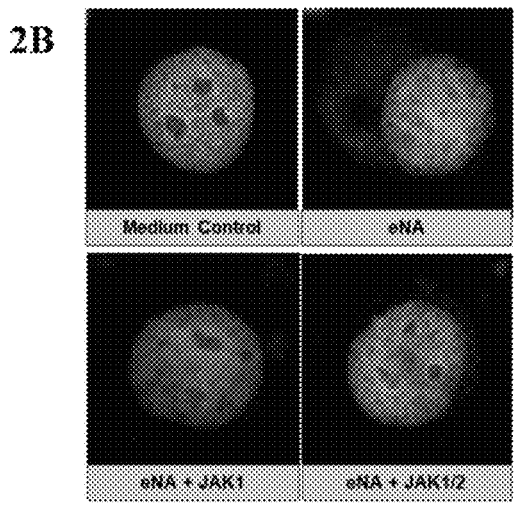

JAK1-phosphorylation was strongly enhanced within immortalized keratinocytes (HaCaT) after stimulation with eNA, corresponding with the findings in CLE skin lesions described above (see Examples 2-3). As shown in FIGS. 2A-2B, JAK-specific INCB039110 and JAK/2-specific ruxolitinib significantly decreased the activation of JAK1 within stimulated cells.

Figure 2C:
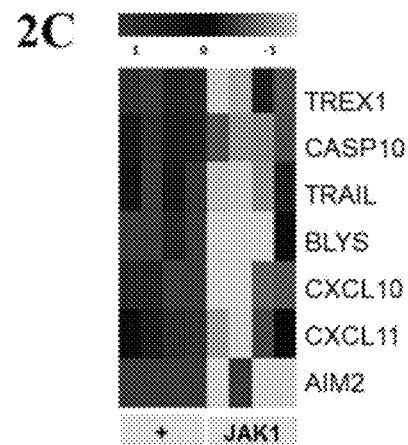

Example 4. Pharmacological JAK1 Inhibition Blocks the Expression of CLE-Typical Proinflammatory Cytokines and Pathway Molecules in Vitro To investigate the efficacy of pharmacological JAK1 inhibition, in vitro analyses in three different CLE-models were performed (i) NHEK-cells, (ii) HaCaT-cells and (iii) 3D epidermis equivalents. As shown in FIG. 2C, pharmacological JAK1 inhibition induced a significant downregulation of genes encoding key drivers of innate inflammatory pathways such as IFN-regulated chemokines (CXCL10, CXCL11), cell death (TRAIL, AIM2, TREX1) and crosstalk to adaptive immune cells (BlyS) within primary keratinocytes (NHEK) compared to untreated eNA-inflamed cells. Associated downregulated KEGG pathways are listed in Table A. These results were confirmed in HaCaT-cells, where both JAK1- and JAK1/2 inhibitors decreased the protein expression of CXCL10 significantly.

TABLE A

| Pathway[a] | KEGG | p-value | Count |
|---|---|---|---|
| Innate Immune System | | | |
| Cytokine-cytokine receptor interaction | hsa04060 | 4.10E−05 | 9 |
| Chemokine signalling pathway | hsa04062 | 2.20E−02 | 5 |
| Toll-like receptor signalling pathway | hsa04620 | 2.30E−02 | 4 |
| Cytosolic DNA-sensing pathway | hsa04623 | 5.30E−02 | 3 |
| Immunometabolism | | | |
| Arachidonic acid metabolism | hsa00590 | 5.40E−03 | 4 |
| alpha-Linolenic acid metabolism | hsa00592 | 9.00E−03 | 3 |
| Linoleic acid metabolism | hsa00591 | 1.20E−02 | 3 |
| Ether lipid metabolism | hsa00565 | 2.80E−02 | 3 |

[a]KEGG pathways were classified using Database for Annotation, Visualization and Integrated Discovery (DAVID ver. 6.8). P-values were generated with EASE Score. Count: number of genes >2-fold downregulated in NHEK by INCB039110 within the respective KEGG pathway.

Figure 2D:
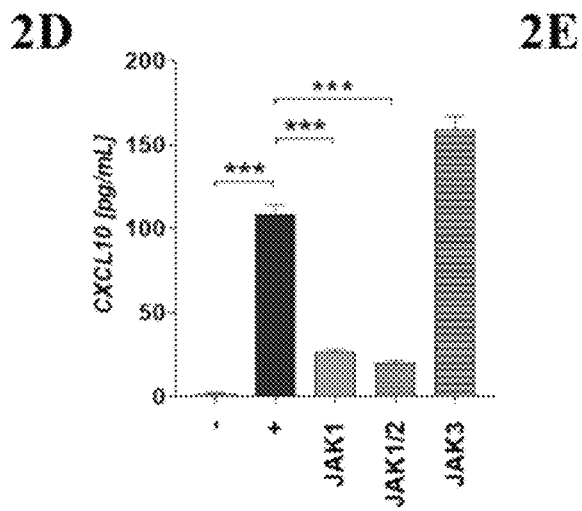

The in vitro data disclosed herein demonstrates that JAK1 selective inhibitors are as potent as JAK1/2 inhibitors in suppression of CLE typical cytokines, as shown in FIG. 2D, and prohibit gene expression encoding proinflammatory chemokines (CXCL10-11), lymphocyte activators (BLyS) (see e.g., Wenzel et al, *Exp. Dermatol.* 2018, 27:95-97) and cell death promotors (TRAIL (see e.g., Zahn et al, *Br. J. Dermatol.* 2011, 165:1118-1123), AIM2, Caspase 10, TREX1). Interestingly, inhibition of JAK3 did not obtain a reduction of CXCL10 expression, as shown in FIG. 2D, which is a central mediator of CLE-typical "interface dermatitis". Without being bound by theory, this could explain the earlier failure of the JAK3/SYK blocking agent R333 in a clinical CLE study (see e.g., Presto et al, *Br. J. Dermatol.*

Figure 2E:
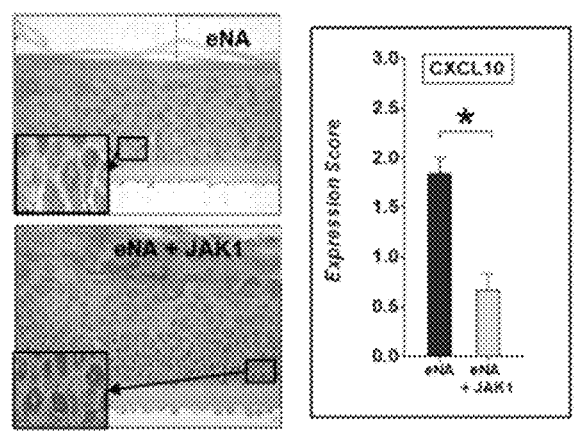

2018, 178:1308-1314). In 3D epidermis equivalents, exposure of a JAK1 selective inhibitor to stimulated epiCS revealed a significantly reduced CXCL10 protein expression, consistent to findings described above, as shown in FIG. 2E.

Example 5. In Vivo Topical Application of INCB039110 Ameliorates CLE-Like Lesions in Lupus-Prone TREX1$^{-/-}$ Mice TREX1$^{-/-}$ mice (generated on C57BL/6J background; Cancer Research Institute, London, UK) were bred and maintained under specific pathogen-free conditions at the animal core facility of UKB Bonn (HET, Bonn, Germany). TREX1$^{-/-}$ mice (n=8) were back-shaved and treated with 0.2% DNFB (1-Fluor-2,4-dinitrobenzol, Sigma Aldrich). 4 days later, UV-irradiation on 3 sequential days started with 450 mJ/cm$^2$ UVB for 115 seconds per day using UV801KL (Waldmann, Villingen-Schwenningen, Germany). For 7 days 1% INCB039110 or vehicle solved in DMSO and olive oil (50 µL per mouse) were applied topically. Every day photos of mice were taken and every 2 days mice were weighed.

Figures 3A, 3B, 3C:
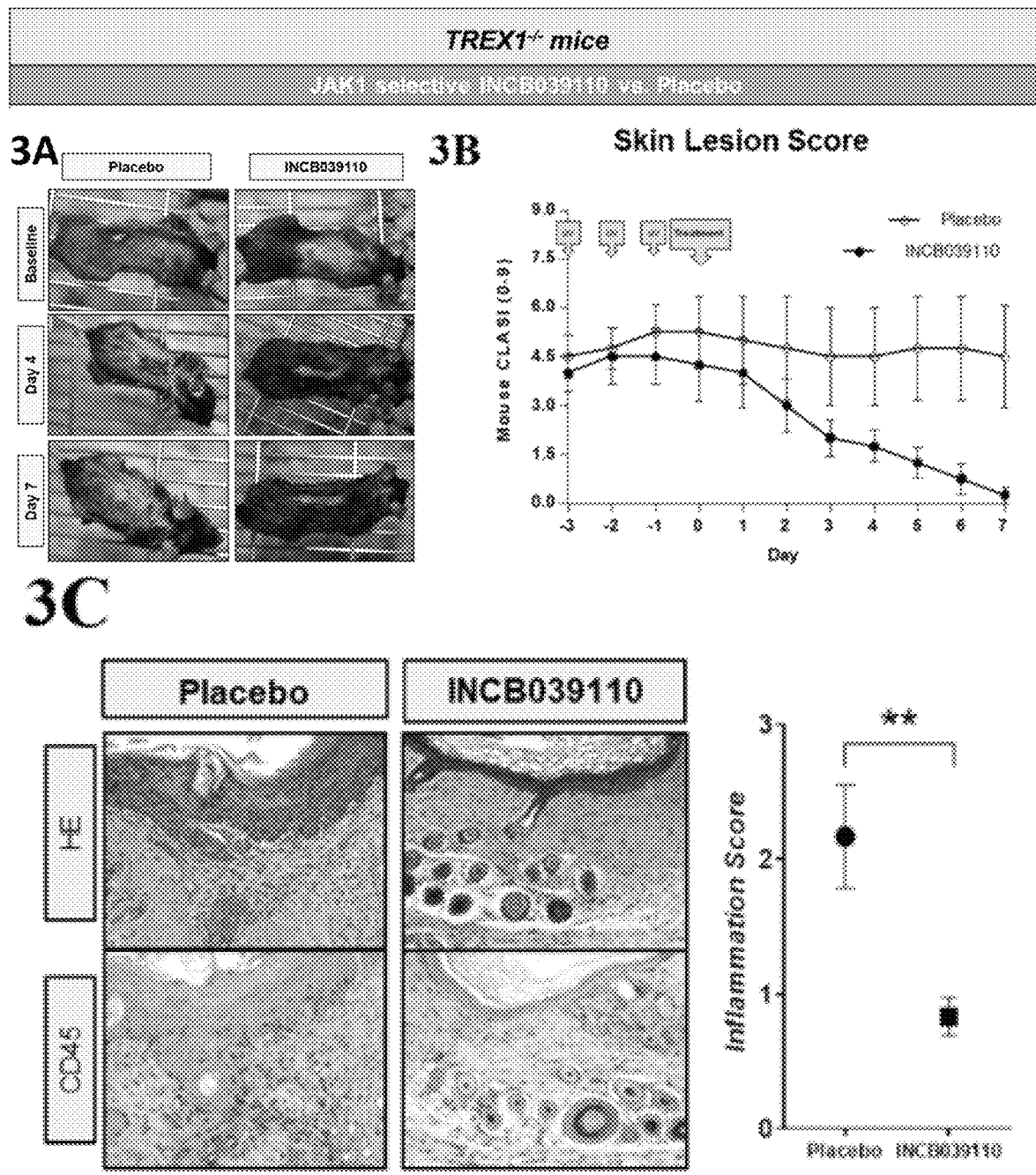
FIGS. 3A-3C show pharmacological JAK1 inhibition in vivo in a lupus-prone TREX1$^{-/-}$ mouse model.

TREX1$^{-/-}$ mice spontaneously developed CLE-like erythrosquamous and partly ulcerated skin lesions at a certain age which intensified after UVB-provocation. Topical treatment with JAK1-specific INCB039110 for seven days continuously improved lesional skin regarding erythema, induration, scaling and size leading to a significantly reduced lupus-skin-activity-score (adapted CLASI score) compared to placebo-treated mice, as shown in FIGS. 3A-3B. In addition, distinct histological features such as epidermal thickness and infiltrating dermal immune cells were significantly improved by JAK1 inhibition, as shown in FIG. 3C.

Figures 4A, 4B, 4C, 4D, 4E, 4F:
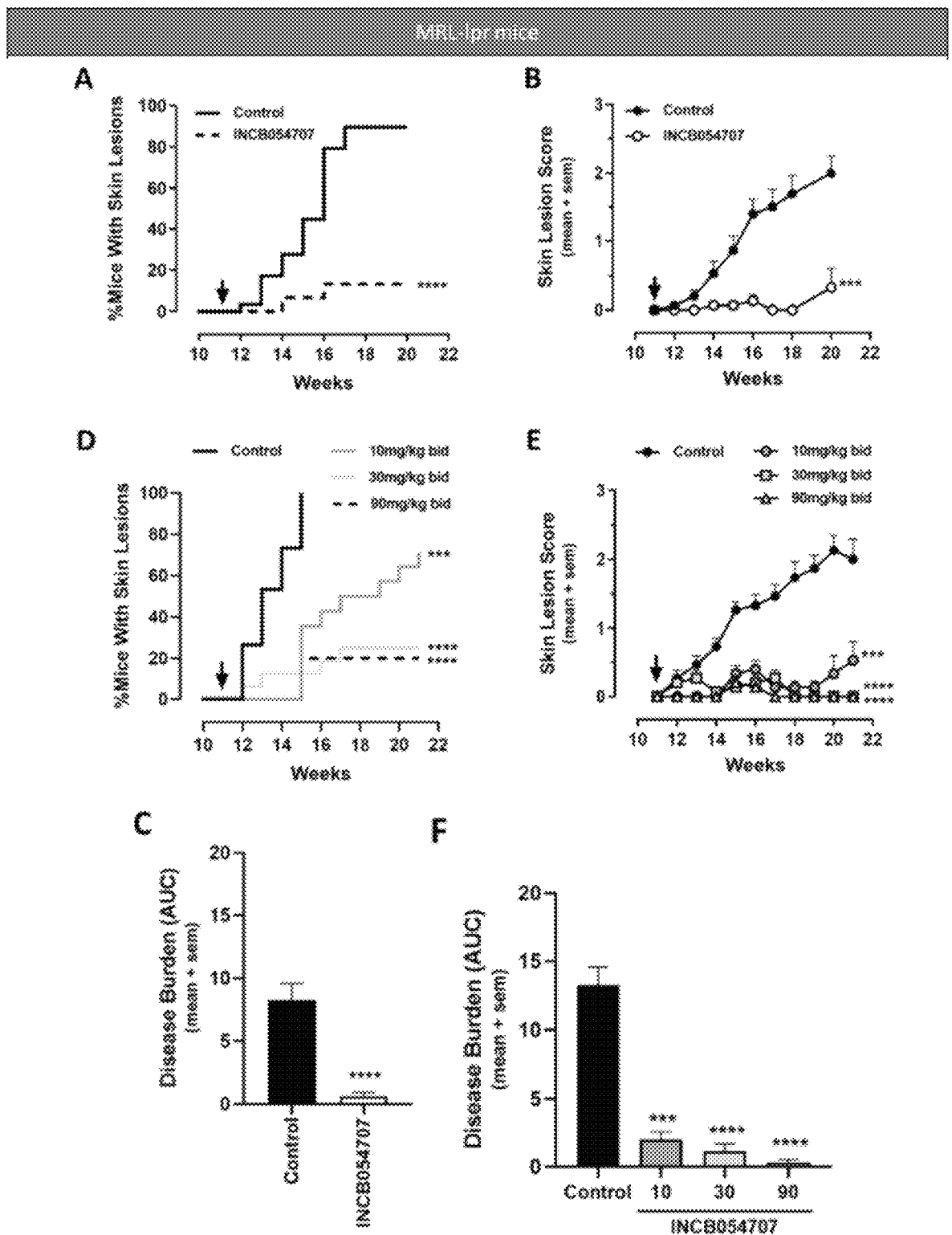
FIGS. 4A-4F show pharmacological JAK1 inhibition in vivo in a lupus-prone MRL-lpr mouse model.

Example 6. In Vivo Topical Application of INCB054707 Ameliorates CLE-Like Lesions in Lupus-Prone MRL-Lpr Mice Topical treatment with JAK1-selective INCB054707 started with the MRL-lpr Mice at 11 weeks of age. Topical treatment with JAK1-selective INCB054707 from 11 weeks to 22 weeks continuously improved lesional skin regarding erythema, induration, scaling and size leading to a significantly reduced cutaneous skin lesion score and a significantly reduced incidence of mice with skin lesions, compared to placebo-treated mice, as shown in FIGS. 4A-4B. In addition, topical treatment with JAK1-selective INCB054707 significantly reduced the cumulative skin lesion disease burden (area under the curve), as shown in FIG. 4C. In another independent experiment using the lupus-prone MRL-lpr mouse model, topical treatment with JAK1-selective INCB054707 showed the significant dose-dependent effects on the daily cutaneous skin lesion score, the incidence of mice with skin lesions, and the cumulative skin lesion disease burden, as shown in FIGS. 4D-4F.

Figures 5A, 5B, 5C:
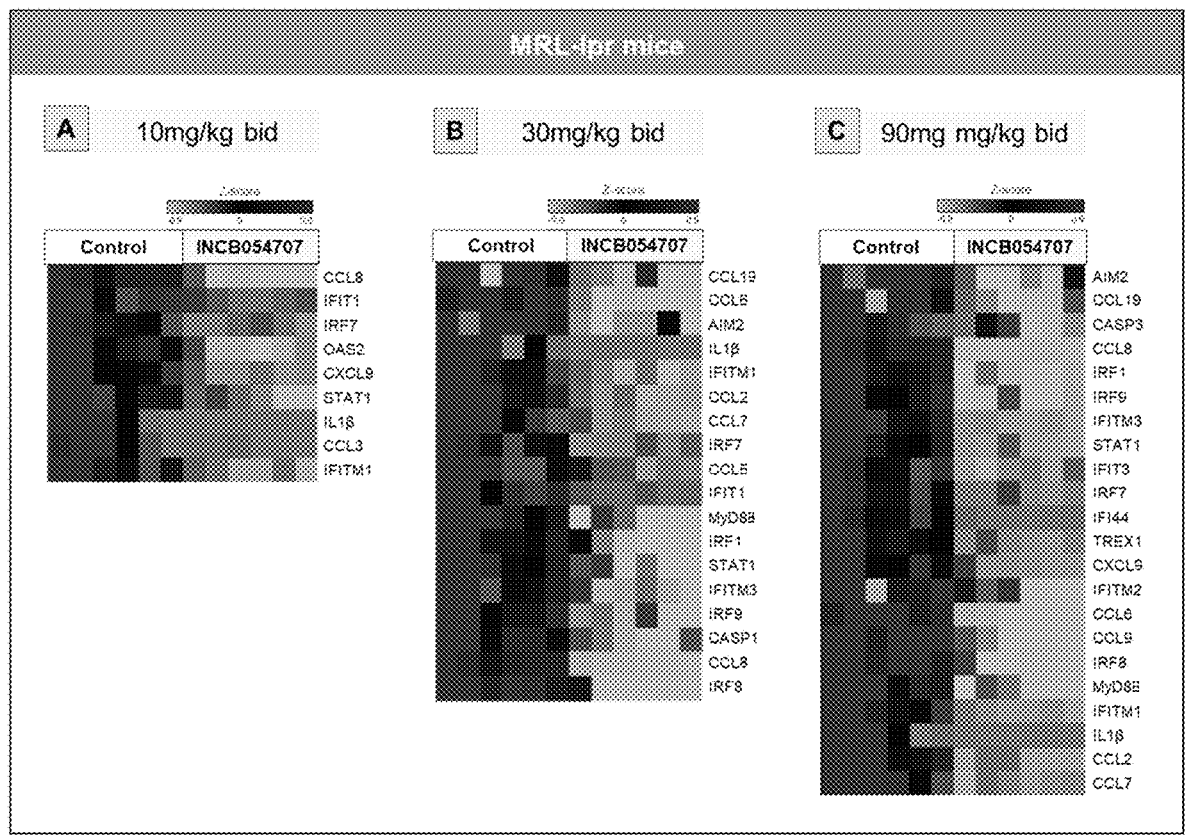
FIGS. 5A-5C show RNAseq heat map of skin biopsy transcriptomic changes following pharmacological JAK1 inhibition in vivo in a lupus-prone MRL-lpr mouse model.

Topical treatment with JAK1-selective INCB054707 on MRL-lpr Mice resulted in downregulation of multiple inflammatory markers, which were demonstrated by the changes on RNAseq heat map of skin biopsy transcriptomic, and such downregulation was dose-dependent, as shown in FIGS. 5A-5C.

The data disclosed in Examples 2-5 demonstrates that JAK1-specific inhibition significantly decreases the expression of CLE-typical proinflammatory cytokines in vitro and in vivo. Topical application of a JAK1 selective inhibitor was highly effective in the treatment of CLE-like lesions in lupus prone mice, supporting their potential use in human CLE.

Various modifications of the invention, in addition to those described herein, will be apparent to those skilled in the art from the foregoing description. Such modifications are also intended to fall within the scope of the appended claims. Each reference cited in the present disclosure, including all patent, patent applications, and publications, is incorporated herein by reference in its entirety.

What is claimed is:

1. A method of treating cutaneous lupus erythematosus (CLE) in a patient in need thereof, comprising administering to the patient a therapeutically effective amount of a JAK1 selective inhibitor, wherein the JAK1 selective inhibitor is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

2. The method of claim 1, wherein the pharmaceutically acceptable salt is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

3. The method of claim 1, further comprising administering to the patient an additional therapeutic agent.

4. The method of claim 3, wherein the additional therapeutic agent is selected from a JAK1/JAK2 inhibitor, a JAK1/JAK3 inhibitor, a TYK2 inhibitor, or a pharmaceutically acceptable salt of any of the aforementioned.

5. The method of claim 4, wherein the additional therapeutic agent is a JAK1/JAK2 inhibitor, or a pharmaceutically acceptable salt thereof.

6. The method of claim 4, wherein the JAK1/JAK2 inhibitor, or a pharmaceutically acceptable salt thereof, is selective for JAK1 and JAK2 over JAK3 and TYK2.

7. The method of claim 4, wherein the JAK1/JAK2 inhibitor is ruxolitinib, or a pharmaceutically acceptable salt thereof.

8. The method of claim 7, wherein the method comprises topical administration of the ruxolitinib, or a pharmaceutically acceptable salt thereof, to the patient.

9. The method of claim 7, wherein the method comprises oral administration of the ruxolitinib, or a pharmaceutically acceptable salt thereof, to the patient.

10. The method of claim 7, wherein the pharmaceutically acceptable salt is ruxolitinib phosphate.

11. The method of claim 4, wherein the JAK1/JAK2 inhibitor is ruxolitinib, or a pharmaceutically acceptable salt thereof, wherein one or more hydrogen atoms are replaced by deuterium atoms.

12. The method of claim 4, wherein the additional therapeutic agent is a JAK1/JAK3 inhibitor, or a pharmaceutically acceptable salt thereof.

13. The method of claim 4, wherein the JAK1/JAK3 inhibitor is tofacitinib, or a pharmaceutically acceptable salt thereof.

14. The method of claim 1, wherein the method comprises topical administration of the JAK1 selective inhibitor to the patient.

15. The method of claim 1, wherein the method comprises oral administration of the JAK1 selective inhibitor to the patient.

16. The method of claim 1, wherein the cutaneous lupus erythematosus (CLE) is selected from subacute cutaneous lupus erythematosus (SCLE) and chronic discoid lupus erythematosus (CDLE).

* * * * *